US007402571B2

(12) United States Patent
Tennenbaum et al.

(10) Patent No.: US 7,402,571 B2
(45) Date of Patent: Jul. 22, 2008

(54) METHODS AND PHARMACEUTICAL COMPOSITIONS FOR HEALING WOUNDS

(75) Inventors: Tamar Tennenbaum, Jerusalem (IL); Sanford Sampson, Rehovot (IL); Toshio Kuroki, Kawasaki (JP); Addy Alt, Raanana (IL); Shlomzlon Shen, Shaarei Tikva (IL)

(73) Assignee: Bar-Ilan University, Ramat Gan (IL)

( * ) Notice: Subject to any disclaimer, the term of this patent is extended or adjusted under 35 U.S.C. 154(b) by 480 days.

(21) Appl. No.: 10/169,801

(22) PCT Filed: Jul. 23, 2001

(86) PCT No.: PCT/IL01/00675

§ 371 (c)(1),
(2), (4) Date: Jul. 9, 2002

(87) PCT Pub. No.: WO02/09639

PCT Pub. Date: Feb. 7, 2002

(65) Prior Publication Data

US 2003/0017969 A1  Jan. 23, 2003

(51) Int. Cl.
    *A61K 31/70* (2006.01)
(52) U.S. Cl. .......................................... 514/44
(58) Field of Classification Search .................. 514/44
    See application file for complete search history.

(56) References Cited

U.S. PATENT DOCUMENTS

| 4,673,649 | A | 6/1987 | Weimar |
| 4,833,257 | A | 5/1989 | Pettit et al. |
| 4,940,660 | A | 7/1990 | Hirai |
| 5,145,679 | A | 9/1992 | Hinson |
| 5,461,030 | A | 10/1995 | Lindenbaum |
| 5,591,709 | A | 1/1997 | Lindenbaum |
| 5,770,228 | A | 6/1998 | Edwards et al. |
| 5,869,037 | A | 2/1999 | Crystal et al. |
| 6,096,288 | A | 8/2000 | Roth |
| 6,319,907 | B1 * | 11/2001 | Ferguson ............. 514/44 |
| 6,403,656 | B1 | 6/2002 | Rivier |
| 6,541,447 | B1 | 4/2003 | Dawson |
| 6,582,713 | B2 | 6/2003 | Newell et al. |
| 6,737,241 | B2 | 5/2004 | Nolan et al. |
| 2002/0119914 | A1 | 8/2002 | Zhu et al. |

FOREIGN PATENT DOCUMENTS

| EP | 0561330 | 9/1993 |
| EP | 0679402 | 2/1995 |
| WO | WO 85/05036 A1 | 11/1985 |
| WO | WO 90/11071 A1 | 10/1990 |
| WO | WO 92/18147 A1 | 10/1992 |
| WO | WO 93/25660 A1 | 12/1993 |
| WO | WO 96/09810 A1 | 4/1996 |
| WO | WO 96/20724 | 7/1996 |
| WO | WO 96/23522 | 8/1996 |
| WO | WO 99/18920 A1 | 4/1999 |
| WO | WO 99/35283 | 7/1999 |
| WO | WO 9935283 A1 * | 7/1999 |
| WO | WO 01/76650 A1 | 10/2001 |
| WO | WO 02/17980 A2 | 3/2002 |
| WO | WO 02/009639 | 7/2002 |
| WO | WO 02/072092 A1 | 9/2002 |
| WO | WO 2005/007072 | 1/2005 |

OTHER PUBLICATIONS

Database on NCBI, Genbank Accession No. L07860 (Aris et al.), Nov. 2, 1993.*
Perletti et al. (Oncogene, 1998; vol. 16, pp. 3345-3348).*
Mischak et al. (Journ, Biol. Chem. 1993, vol. 268(9), pp. 6090-6096).*
Pancreatic and Duodenal Homeobox Gene 1 Induces Expression of Insulin Genes in Liver and Ameliorates Streptozotocin-Induced Hyperglycemia, Ferber et al., Nature Medicine, vol. 6, No. 5, May 2000, pp. 568-572.
Epidermis AS Target for In-Vivo Gene-Therapy, Hengge et al., Journal of Investigative Dermatology, vol. 105, No. 3, Sep. 1995, pp. 448.
Ex Vivo and In Vivo Gene Transfer to the Skin Using Replication-Deficient Recombinant Adenovirus Vectors, Setoguchi, et al., The Journal of Investigative Dermatology, vol. 102, No. 4, Apr. 1994, pp. 415-421.
Induction of Differentiation in Normal Human Keratinocytes by Adenovirus-Mediated Introduction of the η and δ Isoforms of Protein Kinase C, Ohba et al., Molecular and Cellular Biology, Sep. 1998, vol. 18, No. 9, pp. 5199-5207.
Servold, et al, Growth Factor Impact on Wound Healing, Clinics in Podiatric Medicine and Surgery, vol. 8, No. 4, Oct. 1991, pp. 937-953.
Taran, et al., Improved Vitality of Experimental Random Dorsal Skin Flaps in Rats Treated with Enriched Cell Culture Medium, Plastic and Reconstructive Surgery, vol. 104, No. 1, Jul. 1999, pp. 148-151.
Jeschke et al., IGF-I Gene Transfer in Thermally Injured Rats, Gene Therapy, (1999) G. pp. 1015-1020.
Spravchikov, et al., Glucose Effects on Skin Keratinocytes, Implications for Diabetes Skin Complications, Diabetes, vol. 50, Jul. 2001, pp. 1627-1635.
Andre et al., Protein Kinases C-γ and -δ are Involved in Insulin-like Growth Factor I-Induced Migration of Colonic Epithelial Cells, Gastroenterology, 1999;116, pp. 64-77.
Shen et al., PKCδ Activation-A Divergence Point in the Signaling of Insulin and IGF-1-Induced Proliferation of Skin Keratinocytes, Diabetes, vol. 50, Feb. 2001, pp. 255-264.
Pittelkow et al., Serum-free Culture of Normal Human Melanocytes: Growth Kinetics and Growth Factor Requirements, Journal of Cellular Physiology, 140:566-576(1989).

(Continued)

*Primary Examiner*—Jon E. Angell
(74) *Attorney, Agent, or Firm*—Fulbright & Jaworski L.L.P.

(57) ABSTRACT

A pharmaceutical composition and method for inducing or accelerating a healing process of a skin wound are described. The pharmaceutical composition contains, as an active ingredient, a therapeutically effective amount of an agent for either enhancing PKC production and/or enhancing PKC activation; and a pharmaceutically acceptable carrier. The method is effected by administering the composition to a wound.

3 Claims, 16 Drawing Sheets

OTHER PUBLICATIONS

Jeschke, Effect of Multiple Gene Transfers of Insulinlike Growth Factor I Complementary DNA Gene Constructs in Rats After Thermal Injury, Arch Surg. 1999;134:1137-1141.

Bitar et al., Insulin and Glucocorticoid-dependent Suppression of the IGF-I System in Diabetic Wounds, Surgery, vol. 127, No. 6, pp. 687-695, Jun. 2000.

Wertheimer et al., The Regulation of Skin Proliferation and Differentiation in the IR Null Mouse: Implications for Skin Complications of Diabetes, Endocrinology, vol. 142, No. 3, pp. 1234-1241, Mar. 2001.

Braiman, et al., Tyrosine Phosphorylation of Specific Protein Kinase C Isoenzymes Participates in Insulin Stimulation Glucose Transport in Primary Cultures of Rat Sketal Muscle, Diabetes, vol. 48, Oct. 1999, pp. 1922-1929.

Braiman, Protein Kinase Cδ Mediates Insulin-Induced Glucose Transport in Primary Cultures of Rat Skeletal Muscle, Molecule Endocrinology, vol. 13, No. 12, pp. 2002-2012.

Ohba et al., Induction of Differentiation in Normal Human Keratinocytes by Adenovirus-Mediated Introduction of the η and δ Isoforms of Protein Kinase C, Mollecular and Cellular Biology, Sep. 1998, vol. 18, No. 9, pp. 5199-5207.

Lindenbaum et al., Serum-free Cell Culture Medium Induces Acceleration of Wound Healing in Guinea-Pigs, Burns, vol. 21, No. 2, 1995, pp. 110-115.

Spravchikov, et al., The Interactive Effects of Hyperglycemia, Insulin and IFG-1 in Murine Skin Cells-An IR-Null Mouse Model, Dept. of Pathology, Sackler School of Medicine, Tel Aviv University, Israel, (Abstract), Aug. 2000.

Shen, et al., Protein Kinase C Activation: A Divergence Point in the Signaling of Insulin and Insulin Like Growth Factor-1 Induced Proliferation of Skin Keratinocytes, Bar Ilan University, Ramat Gan, Israel, (Abstract), Apr. 2000.

Wertheimer, et al., The Effects of Insulin Signaling on Skin Proliferation and Differentiation—Lessons from the IR- and IRS1 Null Models, Dept. of Pathology, Sackler School of Medicine, Tel Aviv University, Tel Aviv, Israel, (Abstract), Aug. 2000.

Al, et al. "The experimental study of bone marrow mesenchymal stem cells on the repair of skin wound combined with local radiation injury", Zhonhghua Yi Xue Za Zhi, 82(23), (2002), pp. 1632-1636; Pubmed Abstract PMID 12667374.

Alessenko, et al. "Selective changes in protein kinase C isoenzymes in rat liver nuclei during liver regeneration", Biochem. Biophys, Commun., 182, (1992), pp. 1333-1339.

Bajou, et al. "Absence of host plasminogen activator inhibitor 1 prevents cancer invasion and vascularization", Nat. Med., 4 (1998), pp. 923-928.

Bandyopadhyay, et al. "Effects of transiently expressed atypical (ζ, λ), conventional (α, β), and novel (ε, E) [. . ]", Biochem. J., 337 (1999), pp. 461-470.

Benes, et al. "The C2 domain of PKC δ is a phosphotyrosine binding domain", Cell, 121 (2005), pp. 271-280.

Chida, et al. "The η isoform of protein kinase C is localized on rough endoplasmic reticulum", Mol. Cell Biol. 14 (1994), pp. 3782-3790.

Denning, et al. "Specific protein kinase C isozymes mediate the induction of keratinocyte differentiation markers by calcium", Cell Growth Differ., 6 (1995), pp. 149-157.

Dlugosz and Yuspa, "Coordinate changes in gene expression which mark the spinous to granular call transition in epidermis are regulated by protein kinase C" J. Cell. Biol., 120 (1993), pp. 217-225.

Formisano, et al. "In NIH-3T3 fibroblasts, insulin receptor interaction with specific protein kinase C isoforms controls receptor intracellular routing", J. Biol, Chem., 273 (1998), pp. 12197-13202.

Gschwendt "Protein kinase Cδ", Eur. J. Biochem., 259 (1999), pp. 555-564.

Hofmann "The potential for isoenzyme-selective modulation of protein kinase C", The FASEB J., 11 (1997), pp. 649-669.

Madibally, et al. "Influence of insulin therapy on burn wound healing in rats", J. Surg. Res., 109 (2003), pp. 92-100.

Michalik, et al. "Impaired skin wound healing in perioxisome proliferator-activated receptor (PRAR) and PPAR mutant mice", J. Cell. Biol., (154) (2001) pp. 799-814.

Mischak, et al. "Phorbol ester- induced myeloid differentiation is mediated by protein kinase C-α and -δ and not by protein kinase C-βII, -ε, -ξ, and -η", J. Biol. Chem., 268 (1993), pp. 20110-20115.

Mooney, et al. "Tumor necrosis factor and wound healing", Annals of Surgery, 211 (2), (1990) pp. 124-129.

Osada, et al., J. Biol. Chem., 265 (1990), pp. 22434-22440.

Pellegrini, et al. "Cultivation of human keratinocyte stem, cells: current and future clinical applications", Med. Biol. Eng. Comp. 36(6), (1998), pp. 778-790.

Rangwala and Lazar "Adipogenic transcriptional regulation", Annu. Rev. Nutr., (20) (2000), pp. 535-559.

Reynolds, et al. "Down-regulation of langerhans cell protein kinase C-beta isoenzyme expression in inflammatory and hyperplastic dermatoses", Br. J. Dermatol., 133(2), (1995), pp. 157-167 [PMED Abstract 7547380].

Ring, et al. "Systematically and topically administered leptin both accelerate wound healing in diabetic ob/obmice",Endocrin., 141(1), (2000), pp. 446-449.

Soltoff and Toker "Carbachol, substance P, and phorbol ester promote the tyrosine phosphorylation of protein kinase Cδ in salivary gland epithelial cells", J. Biol. Chem., 270 (1995), pp. 13490-13495.

Sun, et al. "Squamous metaplasia of normal and carcinoma in situ of HPV 16-immortalized human endocervical cells", Cancer Res., 52 (1992), pp. 4254-4260.

Tennenbaum, et al. "Selective changes in laminin adhesion and $\alpha_6\beta_4$ integrin regulation are associated with the initial steps in keratinocyte maturation", Cell Growth Differ., 7 (1996), pp. 615-628.

Wang, et al. "Differential localization of protein kinase C δ by phorbol esters and related compounds using a fusion protein with green fluorescent protein", J. Biol. Chem., 274 (1999), pp. 37233-37239.

Wertheimer, et al. "Differential roles of insulin receptor and insulin-like growth factor-1 receptor I differentiation of murine skin keratinocytes", J. Invest. Dermatol., (2000), pp. 24-29.

Yuspa "The pathogenesis of squamous cell cancer: lessons learned form studies of carcinogenesis", Cancer Res., 54 (1994), pp. 1178-1189.

Macfarlane et al. "Glucose Stimulates Translocation of the Homeodomain of Transcription Factor PDX1 From the Cytoplasm to the Nucleus of Pancreatic Bet-Cells", J. Biol. Chem., 274(2): 1001-1016, 1999.

Frank, et al. "Leptin enhances wound re-epithelialization and constitutes a direct function of leptin in skin repair", J. Clin. Investigation, vol. 106, No. 4 (2000), pp. 501-509.

* cited by examiner

METHODS AND PHARMACEUTICAL COMPOSITIONS FOR HEALING WOUNDS

RELATED PATENT APPLICATIONS

This application is a National Phase Application of PCT Application No. IL01/00675, filed 23 Jul. 2001, which claims priority of U.S. application Ser. No. 09/629,970 filed 31 Jul. 2000 now abandoned.

FIELD AND BACKGROUND OF THE INVENTION

The present invention relates to a method and a pharmaceutical composition for inducing and/or accelerating cell proliferation and/or cell differentiation and thereby accelerating the healing process of wounds. More particularly, the present invention relates to the use of enhanced expression and/or activation, e.g., as initiated by membrane translocation, of serine/threonine protein kinases, also known as PKCs, for inducing and/or accelerating cell proliferation and/or cell differentiation and thereby accelerating the healing process of wounds. Such enhanced expression may be effected in accordance with the teachings of the present invention by (i) transformation of wound cells with a PKC expressing construct; (ii) transformation of wound cells with a cis-acting element to be inserted adjacent to, and upstream of, an endogenous PKC gene of the wound cells; (iii) administration of insulin for inducing expression and/or activation of PKC in wound cells; (iv) transformation of wound cells with an insulin expressing construct, when expressed and secreted the insulin produced therefrom serves as an up-regulator for PKC expression and/or activation; (v) transformation of wound cells with a cis-acting element to be inserted adjacent to, and upstream of, the endogenous insulin gene of the wound cells, when expressed and secreted the insulin serves as an up-regulator for PKC expression and/or activation; (vi) implantation of insulin secreting cells to the wound; (vii) transformation of wound cells with a trans-acting factor, e.g., PDX1, for induction of endogenous insulin production and secretion, the insulin serves as an up-regulator for PKC expression and/or activation; and (viii) administration to the wound of a PKC activator.

The present invention, as is realized by any of the above methods, can also be practiced ex-vivo for generation of skin grafts.

The primary goal in the treatment of wounds is to achieve wound closure. Open cutaneous wounds represent one major category of wounds and include burn wounds, neuropathic ulcers, pressure sores, venous stasis ulcers, and diabetic ulcers.

Open cutaneous wounds routinely heal by a process which comprises six major components: (i) inflammation; (ii) fibroblast proliferation; (iii) blood vessel proliferation; (iv) connective tissue synthesis; (v) epithelialization; and (vi) wound contraction. Wound healing is impaired when these components, either individually or as a whole, do not function properly. Numerous factors can affect wound healing, including malnutrition, infection, pharmacological agents (e.g., actinomycin and steroids), advanced age and diabetes [see Hunt and Goodson in Current Surgical Diagnosis & Treatment (Way; Appleton & Lange), pp. 86-98 (1988)].

With respect to diabetes, diabetes mellitus is characterized by impaired insulin signaling, elevated plasma glucose and a predisposition to develop chronic complications involving several distinctive tissues. Among all the chronic complications of diabetes mellitus, impaired wound healing leading to foot ulceration is among the least well studied. Yet skin ulceration in diabetic patients takes a staggering personal and financial cost (29, 30). Moreover, foot ulcers and the subsequent amputation of a lower extremity are the most common causes of hospitalization among diabetic patients (30-33). In diabetes, the wound healing process is impaired and healed wounds are characterized by diminished wound strength. The defect in tissue repair has been related to several factors including neuropathy, vascular disease and infection. However, other mechanisms whereby the diabetic state associated with abnormal insulin signaling impairs wound healing and alter the physiology of skin has not been elucidated.

There is also a common problem of wound healing following surgical procedures in various parts of the body, the surgery succeeds but the opening wound does not heal.

Skin is a stratified squamous epithelium in which cells undergoing growth and differentiation are strictly compartmentalized. In the physiologic state, proliferation is confined to the basal cells that adhere to the basement membrane. Differentiation is a spatial process where basal cells lose their adhesion to the basement membrane, cease DNA synthesis and undergo a series of morphological and biochemical changes. The ultimate maturation step is the production of the cornified layer forming the protective barrier of the skin (1, 2). The earliest changes observed when basal cells commit to differentiate is associated with the ability of the basal cells to detach and migrate away from the basement membrane (3). Similar changes are associated with the wound healing process where cells both migrate into the wound area and proliferative capacity is enhanced. These processes are mandatory for the restructuring of the skin layers and induction of proper differentiation of the epidermal layers.

The analysis of mechanisms regulating growth and differentiation of epidermal cells has been greatly facilitated by the development of culture systems for mouse and human keratinocytes (2,4). In vitro, keratinocytes can be maintained as basal proliferating cells with a high growth rate. Furthermore, differentiation can be induced in vitro following the maturation pattern in the epidermis in vivo. The early events include loss of hemidesmosome components (3,5) and a selective loss of the $\alpha 6\beta 4$ integrin and cell attachment to matrix proteins. This suggests that changes in integrin expression are early events in keratinocyte differentiation. The early loss of hemidesmosomal contact leads to suprabasal migration of keratinocytes and is linked to induction of Keratin 1 (K1) in cultured keratinocytes and in skin (1, 3, 6). Further differentiation to the granular layer phenotype is associated with down regulation of both $\beta 1$ and $\beta 4$ integrin expression, loss of adhesion potential to all matrix proteins and is followed by cornified envelope formation and cell death. Differentiating cells ultimately sloughs from the culture dish as mature squames (2, 7). This program of differentiation in vitro closely follows the maturation pattern of epidermis in vivo.

Recent studies in keratinocytes biology highlights the contribution of Protein Kinase C pathways, which regulate skin proliferation and differentiation. The protein kinase C (PKC) family of serine-threonine kinases plays an important regulatory role in a variety of biological phenomena (8,9). The PKC family is composed of at least 12 individual isoforms which belong to 3 distinct categories: (i) conventional isoforms ($\alpha$, $\beta 1$, $\beta 2$, $\gamma$) activated by $Ca^{2+}$, phorbol esters and diacylglycerol liberated intracellularly by phospholipase C; (ii) novel isoforms ($\delta$, $\epsilon$, $\eta$, $\theta$) which are also activated by phorbol esters and diacylglycerol but not by $Ca^{2+}$; and (iii) atypical ($\zeta$, $\lambda$, $\iota$) members of the family, which are not activated by $Ca^{2+}$ phorbol esters or diacylglycerol.

On activation, most but not all isoforms are thought to be translocated to the plasma membrane from the cytoplasm. The type of isoform and pattern of distribution vary among different tissues and may also change as a function of phenotype. Numerous studies have characterized the structure and function of PKC because of its importance in a wide variety of cellular endpoints of hormone action. Five PKC isoforms—α, δ, ε, η and ζ—have been identified in skin in vivo and in culture. Recent studies have shown that the PKC signal transduction pathway is a major intracellular mediator of the differentiation response (10,11). Furthermore, pharmacological activators of PKC are powerful inducers of keratinocyte differentiation in vivo and in vitro (4, 12), and PKC inhibitors prevent expression of differentiation markers (10).

While conceiving the present invention, it was hypothesized that PKC isoforms over-expression and/or activation may be beneficial for accelerating wound healing processes. The limitations for investigating the role of distinct PKC isoforms in skin cells proliferation and/or differentiation has been hampered as result of the difficulty in introducing foreign genes efficiently into primary cells, by conventional methods. The short life span, differentiation potential and the inability to isolate stable transformants do not allow efficient transduction of foreign genes into primary skin cells.

There is a widely recognized need for, and it would be highly advantageous to have, new approaches for accelerating the processes associated with wound healing. In addition, there is a widely recognized need for, and it would be highly advantageous to have, an efficient method to insert recombinant genes into skin cells which will accelerate cell proliferation and/or differentiation processes and wound healing.

SUMMARY OF THE INVENTION

According to one aspect of the present invention there is provided a method of inducing or accelerating a healing process of a skin wound, the method comprising the step of administering to the skin wound a therapeutically effective amount of an agent for either enhancing PKC production and/or enhancing PKC activation.

According to another aspect of the present invention there is provided a pharmaceutical composition for inducing or accelerating a healing process of a skin wound, the pharmaceutical composition comprising, as an active ingredient, a therapeutically effective amount of an agent for either enhancing is PKC production and/or enhancing PKC activity; and a pharmaceutically acceptable carrier.

According to still another aspect of the present invention there is provided a method of inducing or accelerating a healing process of a skin wound, the method comprising the step of administering to the skin wound a therapeutically effective amount of insulin, so as to induce or accelerate the healing process of the skin wound.

According to yet another aspect of the present invention there is provided a pharmaceutical composition for inducing or accelerating a healing process of a skin wound, the pharmaceutical composition comprising, as an active ingredient, a therapeutically effective amount of insulin and a pharmaceutically acceptable carrier being designed for topical application of the pharmaceutical composition.

According to still another aspect of the present invention there is provided a method of inducing or accelerating a healing process of a skin wound, the method comprising the step of implanting into the skin wound a therapeutically effective amount of insulin secreting cells, so as to induce or accelerate the healing process of the skin wound.

According to yet another aspect of the present invention there is provided a pharmaceutical composition for inducing or accelerating a healing process of a skin wound, the pharmaceutical composition comprising, as an active ingredient, insulin secreting cells, and a pharmaceutically acceptable carrier being designed for topical application of the pharmaceutical composition.

According to an additional aspect of the present invention there is provided a method of inducing or accelerating a healing process of a skin wound, the method comprising the step of transforming cells of the skin wound to produce and secrete insulin, so as to induce or accelerate the healing process of the skin wound.

According to yet an additional aspect of the present invention there is provided a pharmaceutical composition for inducing or accelerating a healing process of a skin wound, the pharmaceutical composition comprising, as an active ingredient, a nucleic acid construct being designed for transforming cells of the skin wound to produce and secrete insulin, and a pharmaceutically acceptable carrier being designed for topical application of the pharmaceutical composition.

According to still an additional aspect of the present invention there is provided a method of inducing or accelerating a healing process of a skin wound, the method comprising the step of transforming cells of the skin wound to produce a protein kinase C, so as to induce or accelerate the healing process of the skin wound According to a further aspect of the present invention there is provided a pharmaceutical composition for inducing or accelerating a healing process of a skin wound, the pharmaceutical composition comprising, as an active ingredient, a nucleic acid construct being designed for transforming cells of the skin wound to produce a protein kinase C, and a pharmaceutically acceptable carrier being designed for topical application of the pharmaceutical composition.

According to still a further aspect of the present invention there is provided a method of inducing or accelerating a healing process of a skin wound, the method comprising the step of administering to the skin wound a therapeutically effective amount of PKC activator, so as to induce or accelerate the healing process of the skin wound.

According to a still further aspect of the present invention there is provided a pharmaceutical composition of inducing or accelerating a healing process of a skin wound, the pharmaceutical composition comprising, as an active ingredient, a therapeutically effective amount of PKC activator, so as to induce or accelerate the healing process of the skin wound, and an acceptable pharmaceutical carrier.

According to further features in preferred embodiments of the invention described below, the wound is selected from the group consisting of an ulcer, a burn, a laceration and a surgical incision.

According to still further features in the described preferred embodiments the ulcer is a diabetic ulcer.

According to still further features in the described preferred embodiments the insulin is recombinant.

According to still further features in the described preferred embodiments the insulin is of a natural source.

According to still further features in the described preferred embodiments the pharmaceutical composition is selected from the group consisting of an aqueous solution, a gel, a cream, a paste, a lotion, a spray, a suspension, a powder, a dispersion, a salve and an ointment.

According to still further features in the described preferred embodiments the pharmaceutical composition includes a solid support.

According to still further features in the described preferred embodiments the cells are transformed to produce and secrete insulin.

According to still further features in the described preferred embodiments the cells are transformed by a recombinant PDX1 gene and therefore the cells produce and secrete natural insulin. According to still further features in the described preferred embodiments the cells are transformed by a cis-acting element sequence integrated upstream to an endogenous insulin gene of the cells and therefore the cells produce and secrete natural insulin.

According to still further features in the described preferred embodiments the insulin secreting cells are capable of forming secretory granules.

According to still further features in the described preferred embodiments the insulin secreting cells are endocrine cells.

According to still further features in the described preferred embodiments the insulin secreting cells are of a human source.

According to still further features in the described preferred embodiments the insulin secreting cells are of a histocompatibility humanized animal source.

According to still further features in the described preferred embodiments the insulin secreting cells secrete human insulin.

According to still further features in the described preferred embodiments the insulin secreting cells are autologous cells.

According to still further features in the described preferred embodiments the cells are selected from the group consisting of fibroblasts, epithelial cells and keratinocytes.

According to still further features in the described preferred embodiments the cells are transformed to produce a protein kinase C transcription activator and therefore the cells produce natural protein kinase C.

According to still further features in the described preferred embodiments the cells are transformed by a cis-acting element sequence integrated upstream to an endogenous protein kinase C of the cells and therefore the cells produce natural protein kinase C.

According to still further features in the described preferred embodiments the cells are transformed by a recombinant protein kinase C gene and therefore the cells produce recombinant protein kinase C.

According to still further features in the described preferred embodiments the protein kinase C is selected from the group consisting of PKC-β1, PKC-β2, PKC-γ, PKC-θ, PKC-λ, and PKC-ι.

According to still further features in the described preferred embodiments the protein kinase C is selected from the group consisting of PKC-α, PKC-δ, PKC-ε, PKC-η and PKC-ζ.

The present invention successfully addresses the shortcomings of the presently known configurations by providing new therapeutics to combat skin wounds.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
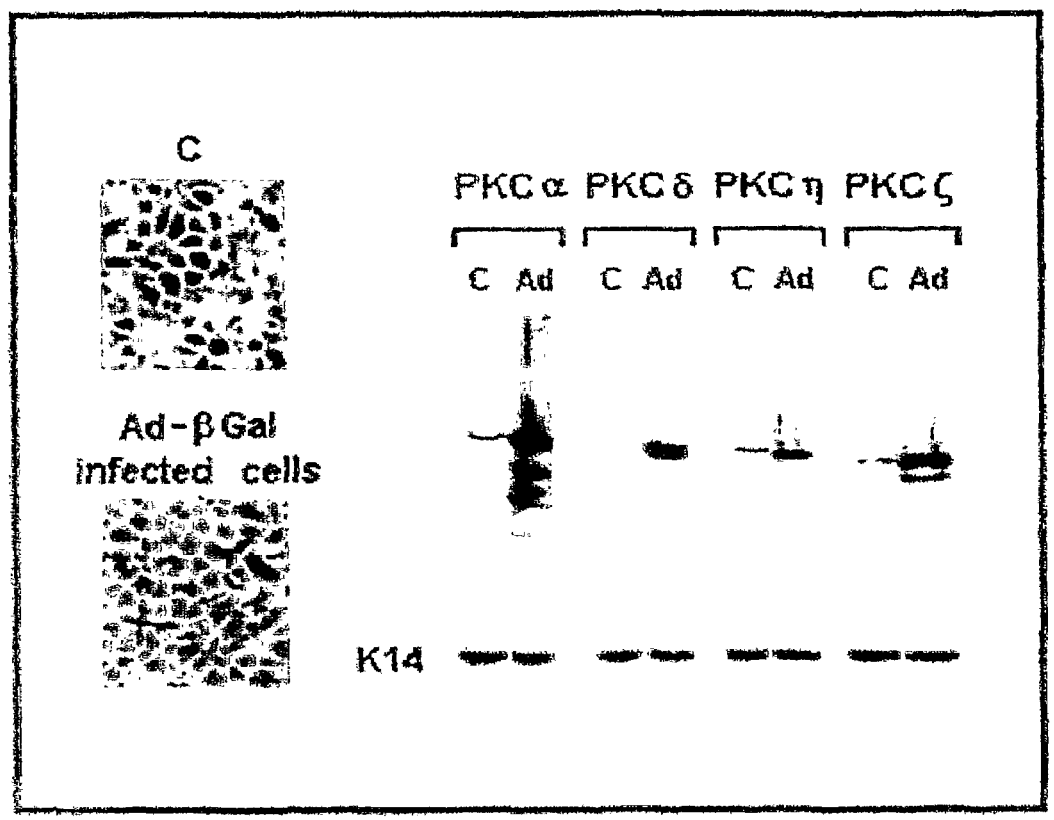
FIG. 1 demonstrates effective over-expression of PKC isoforms utilizing recombinant adenovirus vectors: Left panel: four day old primary keratinocytes were infected for 1 hour utilizing β-gal adenovirus 48 hours following infection, cells were fixed and activation of β-galactosidase protein was quantified by the induction of blue color reaction in comparison to uninfected keratinocytes. Right panel: four day old primary keratinocytes were infected for 1 hour utilizing recombinant isoform specific PKC adenoviruses. Twenty four hours later, proteins of infected (Ad) and non infected control (C) cultures were extracted for Western blot analysis and samples were analyzed using isoform specific anti-PKC antibodies as described in the Examples section below.

The present invention is of methods and pharmaceutical compositions designed for enhancing the expression and/or activation of serine/threonine protein kinases, also known as PKCs, for inducing and/or accelerating cell proliferation and/ or cell differentiation, and thereby accelerate the healing process of wounds. Such enhanced expression may be effected in accordance with the teachings of the present invention by, for example, (i) transformation of wound cells with a PKC expressing construct; (ii) transformation of wound cells with a cis-acting element to be inserted adjacent to, and upstream of, an endogenous PKC gene of the wound cells; (iii) administration of insulin for inducing the expression and/or activation of PKC in wound cells; (iv) transformation of wound cells with an insulin expressing construct, when expressed and secreted the insulin produced therefrom serves as an up-regulator for PKC expression and/or activation; (v) transformation of wound cells with a cis-acting element to be inserted adjacent to, and upstream of, the endogenous insulin gene of the wound cells, when expressed and secreted the insulin serves as an up-regulator for PKC expression and/or activation; (vi) implantation of insulin secreting cells to the wound; (vii) transformation of wound cells with a trans-acting factor, e.g., PDX1, for induction of endogenous insulin production and secretion, the insulin serves as an up-regulator for PKC expression and/or activation; and (viii) administration to the wound of a PKC activator.

The principles and operation of the methods and pharmaceutical compositions according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or exemplified in the Examples section. The invention is capable of other embodiments or of being practiced or carried out in various ways. Also, it is to be understood that the phraseology and terminology employed herein is for the purpose of description and should not be regarded as limiting.

Adult skin includes two layers: a keratinized stratified epidermis and an underlying thick layer of collagen-rich dermal connective tissue providing support and nourishment. Skin serves as the protective barrier against the outside world. Therefore any injury or break in the skin must be rapidly and efficiently mended. As described in the Background section hereinabove, the first stage of the repair is achieved by formation of the clot that plugs the initial wound. Thereafter, inflammatory cells, fibroblasts and capillaries invade the clot to form the granulation tissue. The following stages involve re-epithelization of the wound where basal keratinocytes have to lose their hemidesmosomal contacts, keratinocytes migrate upon the granulation tissue to cover the wound. Following keratinocyte migration, keratinocytes enter a proliferative boost, which allows replacement of cells lost during the injury. After the wound is covered by a monolayer of keratinocytes, new stratified epidermis is formed and the new basement membrane is reestablished (20-23). Several growth factors have been shown to participate in this process including EGF family of growth factors, KGF, PDGF and TGFβ1 (22-24). Among these growth factors both EGF and KGF are thought to be intimately involved in the regulation of proliferation and migration of epidermal keratinocytes (25,26). Fundamental to the understanding of wound healing biology is a knowledge of the signals that trigger the cells in the wound to migrate, proliferate, and lay down new matrix in the wound gap.

To facilitate understanding of the invention set forth in the disclosure that follows, a number of terms are defined below.

The term "wound" refers broadly to injuries to the skin and subcutaneous tissue initiated in any one of a variety of ways (e.g., pressure sores from extended bed rest, wounds induced by trauma, cuts, ulcers, burns and the like) and with varying characteristics. Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "partial thickness wound" refers to wounds that encompass Grades I-III; examples of partial thickness wounds include burn wounds, pressure sores, venous stasis ulcers, and diabetic ulcers.

The term "deep wound" is meant to include both Grade III and Grade IV wounds.

The term "healing" in respect to a wound refers to a process to repair a wound as by scar formation.

The phrase "inducing or accelerating a healing process of a skin wound" refers to either the induction of the formation of granulation tissue of wound contraction and/or the induction of epithelialization (i.e., the generation of new cells in the epithelium). Wound healing is conveniently measured by decreasing wound area.

The present invention contemplates treating all wound types, including deep wounds and chronic wounds.

The term "chronic wound" refers to a wound that has not healed within thirty days.

The phrase "transforming cells" refers to a transient or permanent alteration of a cell's nucleic acid content by the incorporation of exogenous nucleic acid which either integrates into the cell genome and genetically modifies the cell or remains unintegrated.

The term "cis-acting element" is used herein to describe a genetic region that serves as an attachment site for DNA-binding proteins (e.g., enhancers, operators and promoters) thereby affecting the activity of one or more genes on the same chromosome.

The phrase "trans-acting factor" is used herein to describe a factor that binds to a cis-acting element and modulates its activity with respect to gene expression therefrom. Thus, PDX1 is a trans-acting factor which binds to the insulin gene promoter and modulates its activity.

The phrase "transcription activator" is used herein to describe a factor that increases gene expression. A trans-acting factor is an example of a direct transcription activator.

The term "activator" is used herein to describe a molecule that enhances an activity.

PKC is a major signaling pathway, which mediates keratinocyte proliferation and differentiation. PKC isoforms α, δ, ε, η and ζ are expressed in the skin (4, 10). While conceiving the present invention it was hypothesized that PKC enhanced expression and/or activation may induce cell proliferation and/or cell differentiation and thereby accelerate the healing process of wounds. While reducing the present invention to practice this theory has been approved by numerous experiments showing that PKC enhanced expression and/or activation indeed induces cell proliferation and cell differentiation and accelerates the healing process of wounds. As is further delineated herein in great detail, various distinct approaches were undertaken to enhance expression and/or activation of PKC to thereby accelerate the healing process of wounds. Based on the experimental findings, other approaches have been devised. A striking and novel phenomenon was discovered while reducing the present invention to practice—insulin serves as an inducer for enhanced expression and/or activation of PKC. As such, insulin may serve as a therapeutic agent for topical administration to wounds.

The characteristics of distinct PKC isoforms and their specific effects on cell proliferation and/or differentiation are of great importance to the biology of skin wound healing. Utilizing PKC adenovirus constructs enabled to identify the specific roles of a variety of PKC isoforms in the wound healing process in vitro and in vivo. All isoforms were able to specifically affect different aspects of keratinocyte growth and differentiation. Two isoforms, PKCδ and PKCζ, could specifically regulate integrin regulation (see Example 6 below), adherence to the basement membrane (see Example 9 below) and hemidesmosome formation (see Example 8 below). Two isoforms, PKCδ and PKCη, were found to regulate the proliferation potential of epidermal keratinocytes (see Examples 7 and 11 below). In addition, a dominant negative isoform of PKCη (DNPKCη) was able to specifically induce differentiation in actively proliferating keratinocytes (see Example 12 below). Finally, the importance of distinct PKC isoforms to the wound healing process in skin was also verified in an in vivo system. Utilizing PKC null mice where expression of distinct PKC isoforms was abolished it is shown herein that PKCδ and PKCζ which were found to be required for both adhesion and motility processes in skin keratinocytes are also important in the in vivo wound healing process in an animal model (see Example 19). Whole skin full thickness biopsies in PKC null skin suggested that both PKCδ and PKCζ but not PKCα are essential for proper healing of the wound.

PKCη has a unique tissue distribution. It is predominantly expressed in epithelial tissues (27,28). In situ hybridization studies as well as immunohistochemical studies have demonstrated PKCη is highly expressed in the differentiating and differentiative layers (27). The results presented herein suggest the role of PKCη as a functional regulator of both proliferation and differentiation of skin depending on the cellular physiology. When keratinocytes are maintained in a proliferative state under low $Ca^{2+}$ conditions, PKCη induced the proliferation rate five to seven times above control keratinocytes. However, when cells were induced to differentiate by elevating the $Ca^{2+}$ concentration, differentiation was induced in a faster and higher rate in comparison to control cells (see Example 12). This could explain the ability of PKCη to dramatically induce wound healing and formation of granulation tissue as both proliferative capacity and formation of differentiation layers were achieved. Interestingly, the wound healing results in vivo and the expression of PKCη in embryonic tissue, which normally does not express PKCη at high levels in adulthood, would suggest a possible role for PKCη in the proliferation and tissue organization of other tissues as well. This includes neuronal as well as dermal and muscle tissue, which were efficiently healed in the granulation tissue of the wound. Furthermore, the ability to specifically regulate differentiation of keratinocytes and induce normal differentiation in actively proliferating cells by utilizing a dominant negative mutant allows specifically to manipulate differentiation and control hyperproliferative disorders involved in wound healing.

It is exemplified herein that the healing ability of PKCη is exerted in vivo, on wounds that were produced on the backs of nude mice. Example 14 below shows that administration of PKCη expressing construct to the wound resulted in a granulation tissue formation, four days after topical infection.

Overall, the results presented herein demonstrate that expression and activation (membrane mobilization) of PKC isoforms is an effective tool to combat persistent wounds.

Thus, according to one aspect of the present invention there is provided a method of inducing or accelerating a healing process of a skin wound, the method is effected by administering to the skin wound a therapeutically effective amount of an agent for either enhancing PKC production and/or enhancing PKC activation. A pharmaceutical composition for effecting the method according to this aspect of the present invention therefore includes, as an active ingredient, a therapeutically effective amount of an agent for either enhancing PKC production and/or enhancing PKC activation; and a pharmaceutically acceptable carrier.

Skin is not considered to be a classic insulin responsive tissue. Therefore, the effects of insulin in skin are mostly attributed to its ability to activate the closely related IGFR. It was shown that in keratinocytes, both insulin and IGF1 can stimulate both receptors and activate similar downstream effectors (34). However, the present invention demonstrates that whereas both growth factors induce keratinocyte proliferation in a dose-dependent manner, each hormone exerts its effects through distinct signaling pathways. The initial indication for differential regulation of keratinocyte proliferation by insulin and IGF1 was confirmed by the finding that these hormones had an additive effect on keratinocyte proliferation when added together, at maximal proliferation-inducing concentration of each hormone (see Example 15). In order to identify the divergence point in insulin and IGF1 signaling pathway in regulation of keratinocyte proliferation, elements known to both regulate keratinocyte proliferation and to act as downstream effectors of insulin signaling were examined. These studies revealed that insulin signaling is specifically mediated by PKCδ in keratinocyte proliferation (see Example 17). PKCδ is a unique isoform among the PKC family of proteins involved specifically in growth and maturation of various cell types (35). However, while PKCδ was shown to be specifically regulated by stimulation of several growth factors including EGF, Platelet derived growth factor and neurotransmitters, its physiological effects were shown to participate in growth factor inhibition of cell growth including apoptosis, differentiation, and cell cycle retardation or arrest (36-41). Recently it was shown that within 12-24 hours after elevation of $Ca^{2+}$, a selective loss of the α6β4 integrin complex is linked to induction of the K1 in cultured mouse keratinocytes (6). The loss of α6β4 protein expression is a consequence of transcriptional and post-translational events including enhanced processing of the α6 and β4 chains. In preliminary studies a link was established between the activation of PKC and the processing and regulation of the α6β4 integrin. These results are in agreement with previous results on the role of PKCδ as well as PKCζ in loss of α6β4 expression and hemidesmosome formation inducing keratinocyte detachment. However, the present invention identifies another role for PKCδ, as a target for insulin induced keratinocyte proliferation. The examples below show that only insulin stimulation, but not a variety of growth factors, including, but not limited to, EGF, KGF, PDGF, ECGF and IGF1, can translocate and activate PKCδ, but not any of the other PKC isoforms expressed in skin. The importance of PKCδ to insulin stimulation was further confirmed when the mitogenic stimulation by EGF, KGF, PDGF, ECGF and IGF1 were not abrogated by the dominant negative mutant of PKCδ and insulin appeared to be the primary activator of this PKC isoform in the regulation of keratinocyte proliferation (see Example 17). However, when keratinocytes were infected with WT PKCδ keratinocytes mitogenic stimulation by EGF and KGF was enhanced. This suggests that PKCδ activation is also essential for the proliferative stimulation of other growth factors by upstream signaling pathways. Moreover, down stream elements were characterized which meidate in insulin induced PKCδ activation and keratinocyte proliferation and the involvement of STAT3, a transcriptional activator in this process, was identified. STAT (Signal Transducers and Activators of Transcription) proteins are a family of transcription factors recruited by a variety of cytokines and growth factors. Among the seven known STAT family members STAT3 is unique. Targeted disruption of STAT3 but not other STAT family members leads to early embryonic lethality. Specifically, when STAT3 was conditionally ablated in skin, skin remodeling was severely disrupted. Upon activation, STAT proteins form homo or heterodimers, translocate to the nucleus and bind to DNA response elements of target genes to induce transcription. It was found that in keratinocytes, PKCδ but not other PKC isoforms expressed in skin (PKCs α, ζ, η and ε) is constitutively associated with STAT3 (see, Example 18). Furthermore, insulin regulates phosphorylation, activation and nuclear translocation of STAT3 via specific activation of PKCδ. Inhibition of PKCδ activity by a pharmacological inhibitor, rottlerin or by overexpressing a dominant negative PKCδ mutant abrogated insulin induced STAT3 activation and nuclear translocation. Finally, overexpression of a dominant negative PKCδ mutant inhibited keratinocyte proliferation induced by overexpression of STAT3 (see, Example 18). These results suggest a role for insulin induced PKCδ activity in transcriptional activation by STAT3 in skin keratinocyte proliferation. As STAT3 is important for skin remodeling and is a down stream effector recruited by a variety of cytokines and growth factors, overall these results suggest PKCδ activation as a primary downstream element mediating the proliferation of keratinocytes by a variety of skin growth factors. Specifically, PKCδ could be the primary candidate for the pathogenesis of defective wound healing as it appears in diabetic patients. The link between PKCδ and wound healing was also been coroborated in vivo. Utilizing a newly constructed PKCδ null mouse it is shown herein that the lack of PKCδ, delays wound healing in mice skin (see Example 19). The link between PKCδ and insulin signaling has also been established in several other systems. For example, it was recently shown that in muscle cultures, PKCδ mediates insulin-induced glucose transport (42, 43). Similarly, in cells over-expressing the insulin receptor, insulin stimulation was shown to be associated with activation of PKCδ (44-46). However, whereas in these studies insulin mediated PKCδ activation has been linked to the metabolic effects of insulin, this is the first report linking PKCδ to insulin mediated cell proliferation. An identified dual role for PKCδ in regulation of both keratinocyte proliferation and the control of the early differentiation stages where cells lose their adherence to the underlying basement membrane was shown. This would suggest insulin induced PKCδ as a primary candidate of regulation of physiological balance between proliferation and differentiation in skin.

Thus, in accordance with the teachings of the present invention enhancing PKC production and/or enhancing PKC activation is effected by subjecting wound cells to insulin. This can be executed by one of a plurality of alternative ways as is further exemplified hereinunder.

One way is the direct administration of insulin to the wound. Thus, according to another aspect of the present invention there is provided a method of inducing or accelerating a healing process of a skin wound. The method is effected by administering to the skin wound a therapeutically effective amount of insulin, so as to induce or accelerate the healing process of the skin wound. A pharmaceutical composition for inducing or accelerating a healing process of a skin wound, according to this aspect of the present invention therefore includes, as an active ingredient, a therapeutically effective amount of insulin and a pharmaceutically acceptable carrier designed for topical application of the pharmaceutical composition, such as, but not limited to a gel, a cream, a paste, a lotion, a spray, a suspension, a powder, a dispersion, a salve and an ointment, as is further detailed hereinunder. Solid supports can also be used for prolonged release of insulin into the wound. It will be appreciated that the insulin can be native or preferably recombinant, of a human or any other suitable source.

In an alternative embodiment of the present invention, cells expressing and secreting insulin are implanted into the wound, so as to induce or accelerate the healing process of the skin wound. Such insulin producing cells may be cells naturally producing insulin, or alternatively, such cells are transformed to produce and secrete insulin. The cells can be transformed by, for example, a recombinant PDX1 gene (see GeneBank Accession Nos. AH005712, AF035260, AF035259) which is a trans-acting factor for the production and secretion of insulin. Alternatively, the cells can be transformed by a cis-acting element sequence, such as a strong and constitutive or inducible promoter integrated upstream to an endogenous insulin gene of the cells, by way of gene knock-in, so as to transform the cells to overproduce and secrete natural insulin. This is obtainable because the upstream regions of the insulin gene have been cloned (See Accession Nos. E00011, NM000207). Alternatively, the cells are transformed by a recombinant insulin gene (e.g., Accession No. J02547) and therefore the cells produce and secrete recombinant insulin.

A pharmaceutical composition for inducing or accelerating a healing process of a skin wound according to this aspect of the present invention therefore includes, as an active ingredient, insulin secreting cells, and a pharmaceutically acceptable carrier which is designed for topical application of the pharmaceutical composition. Advantageously, the insulin secreting cells administered to a wound are capable of forming secretory granules, so as to secrete insulin produced thereby. The insulin secreting cells can be endocrine cells. They can be of a human source or of a histocompatibility humanized animal source. Most preferably, the insulin secreting cells, either transformed or not, are of an autologous source. The insulin secreted by the insulin secreting cells is preferably human insulin or has the amino acid sequence of human insulin. The insulin secreting cells can be fibroblasts, epithelial cells or keratinocytes, provided that a transformation as described above is employed so as to render such cells to produce and secrete insulin.

In still an alternative embodiment, cells of the skin wound are transformed to produce and secrete insulin, so as to induce or accelerate the healing process of the skin wound.

A pharmaceutical composition for inducing or accelerating a healing process of a skin wound according to this aspect of the present invention therefore includes, as an active ingredient, a nucleic acid construct designed for transforming cells of the skin wound to produce and secrete insulin, and a pharmaceutically acceptable carrier designed for topical application of the pharmaceutical composition.

Any one of the transformation methods described above, e.g., transformation with a construct encoding insulin, transformation with a construct harboring a cis-acting element for insertion downstream of an endogenous insulin gene by way of gene knock-in, and transformation with a construct encoding a trans-acting factor for activation of endogenous insulin production and secretion, can be employed in context of this embodiment of the present invention.

Previous studies on the effects of distinct PKC isoforms in skin have been hampered as a result of the difficulty in introducing foreign genes efficiently into primary cells by conventional methods due to the short life span, differentiation potential and the inability to isolate stable transformants. To overcome these obstacles, viral vectors are being used to introduce genes of interest. Viral vectors are developed by modification of the viral genome in the form of replicative defective viruses. The most widely used viral vectors are the retroviruses and adenoviruses, which are used for experimental as well as gene therapy purposes (13). Specifically, the high efficiency of adenovirus infection in non replicating cells, the high titer of virus and the high expression of the transduced protein makes this system highly advantageous to primary cultures compared to retroviral vectors. As adenoviruses do not integrate into the host genome and the stable viral titers can be rendered replication deficient, these viral constructs are associated with minimal risk for malignancies in human as well as animal models (14). To date, in skin, adenovirus constructs have also been used successfully with high efficiency of infection with ex vivo and in vivo approaches (15, 16). An adenovirus vector, which was developed by I. Saito and his associates (17) was used in the present study. The cosmid cassette (pAxCAwt) has nearly a full length adenovirus 5 genome but lacks E1A, E1B and E3 regions, rendering the virus replication defective. It contains a composite CAG promoter, consisting of the cytomegalovirus immediate-early enhancer, chicken β-actin promoter, and a rabbit β-globin polyadenylation signal, which strongly induces expression of inserted DNAs (13, 17). A gene of interest is inserted into the cosmid cassette, which is then co-transfected into human embryonic kidney 293 cells together with adenovirus DNA terminal protein complex (TPC). In 293 cells that express E1A and E1B regions, recombination occurs between the cosmid cassette and adenovirus DNA-TPC, yielding the desired recombinant virus at an efficiency one hundred fold that of conventional methods. Such high efficiency is mainly due to the use of the adenovirus DNA-TPC instead of proteinesed DNA. Furthermore, the presence of longer homologous regions increases the efficiency of the homologous recombination. Regeneration of replication competent viruses is avoided due to the presence of multiple EcoT221 sites. It should be noted in this respect that keratinocytes were infected with distinct PKC recombinant adenoviruses, demonstrated 24 hours later effective over-expression of PKC isoforms (see example 1).

Thus, another way by which enhancing PKC production and/or enhancing PKC activation is effected according to the present invention is by inducing over-expression of a PKC in the skin wound cells. This can be achieved by transforming the cells with a cis-acting element sequence integrated, by way of homologous recombination, upstream to an endogenous protein kinase C of the cells and thereby causing the cells to produce natural protein kinase C. Still alternatively, this can be achieved by transforming the cells with a recombinant protein kinase C gene, such as, but not limited to, PKC-$\beta$1 gene (Accession Nos. X06318, NM002738), PKC-$\beta$2 gene (Accession No. X07109), PKC-$\gamma$ gene (Accession No. L28035), PKC-$\theta$ gene (Accession No. L07032), PKC-$\lambda$ gene (Accession No. D28577), PKC-$\iota$ gene (Accession No. L18964), PKC-$\alpha$ gene (Accession No. X52479), PKC-$\delta$ gene (Accession Nos. L07860, L07861), PKC-$\epsilon$ gene (Accession No. X72974), PKC-$\eta$ gene (Accession No. Z15108) and PKC-$\zeta$ gene (Accession Nos. Z15108, X72973, NM002744), and thereby causing the cells to produce recombinant protein kinase C.

A pharmaceutical composition for inducing or accelerating a healing process of a skin wound according to this aspect of the present invention therefore includes, as an active ingredient, a nucleic acid construct designed for transforming cells of the skin wound to produce a protein kinase C, and a pharmaceutically acceptable carrier designed for topical application of the pharmaceutical composition.

Still another way by which enhancing PKC production and/or enhancing PKC activation is effected according to the present invention is by a PKC activator, such as, but not limited to $Ca^{2+}$, insulin or bryostatin 1, so as to induce or accelerate the healing process of the skin wound.

A pharmaceutical composition of inducing or accelerating a healing process of a skin wound according to this aspect of the present invention therefore includes, as an active ingredient, a therapeutically effective amount of a PKC activator, so as to induce or accelerate the healing process of the skin is wound, and an acceptable pharmaceutical carrier.

The therapeutically/pharmaceutically active ingredients of the present invention can be administered to a wound per se, or in a pharmaceutical composition mixed with suitable carriers and/or excipients. Pharmaceutical compositions suitable for use in context of the present invention include those compositions in which the active ingredients are contained in an amount effective to achieve an intended therapeutic effect.

As used herein a "pharmaceutical composition" refers to a preparation of one or more of the active ingredients described herein, either protein, chemicals, nucleic acids or cells, or physiologically acceptable salts or prodrugs thereof, with other chemical components such as traditional drugs, physiologically suitable carriers and excipients. The purpose of a pharmaceutical composition is to facilitate administration of a compound or cell to an organism. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Hereinafter, the phrases "physiologically suitable carrier" and "pharmaceutically acceptable carrier" are interchangeably used and refer to a carrier or a diluent that does not cause significant irritation to an organism and does not abrogate the biological activity and properties of the administered conjugate.

Herein the term "excipient" refers to an inert substance added to a pharmaceutical composition to further facilitate processes and administration of the active ingredients. Examples, without limitation, of excipients include calcium carbonate, calcium phosphate, various sugars and types of starch, cellulose derivatives, gelatin, vegetable oils and polyethylene glycols.

Techniques for formulation and administration of active ingredients may be found in "Remington's Pharmaceutical Sciences," Mack Publishing Co., Easton, Pa., latest edition, which is incorporated herein by reference.

While various routes for the administration of active ingredients are possible, and were previously described, for the purpose of the present invention, the topical route is preferred, and is assisted by a topical carrier. The topical carrier is one, which is generally suited for topical active ingredients administration and includes any such materials known in the art. The topical carrier is selected so as to provide the composition in the desired form, e.g., as a liquid or non-liquid carrier, lotion, cream, paste, gel, powder, ointment, solvent, liquid diluent, drops and the like, and may be comprised of a material of either naturally occurring or synthetic origin. It is essential, clearly, that the selected carrier does not adversely affect the active agent or other components of the topical formulation, and which is stable with respect to all components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. Preferred formulations herein are colorless, odorless ointments, liquids, lotions, creams and gels.

Ointments are semisolid preparations, which are typically based on petrolatum or other petroleum derivatives. The specific ointment base to be used, as will be appreciated by those skilled in the art, is one that will provide for optimum active ingredients delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be made to Remington: The Science and Practice of Pharmacy for further information.

Lotions are preparations to be applied to the skin surface without friction, and are typically liquid or semiliquid preparations, in which solid particles, including the active agent, are present in a water or alcohol base. Lotions are usually suspensions of solids, and may comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like.

Creams containing the selected active ingredients are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington, supra, is generally a non-ionic, anionic, cationic or amphoteric surfactant.

Gel formulations are preferred for application to the scalp. As will be appreciated by those working in the field of topical active ingredients formulation, gels are semisolid, suspension-type systems. Single-phase gels contain organic macromolecules distributed substantially uniformly throughout the carrier liquid, which is typically aqueous, but also, preferably, contains an alcohol and, optionally, an oil.

Carriers for nucleic acids include, but are not limited to, liposomes including targeted liposomes, nucleic acid complexing agents, viral coats and the like. However, transformation with naked nucleic acids may also be used.

Various additives, known to those skilled in the art, may be included in the topical formulations of the invention. For example, solvents may be used to solubilize certain active ingredients substances. Other optional additives include skin permeation enhancers, opacifiers, anti-oxidants, gelling agents, thickening agents, stabilizers, and the like.

As has already been mentioned hereinabove, topical preparations for the treatment of wounds according to the present invention may contain other pharmaceutically active agents or ingredients, those traditionally used for the treatment of such wounds. These include immunosuppressants, such as cyclosporine, antimetabolites, such as methotrexate, corticosteroids, vitamin D and vitamin D analogs, vitamin A or its analogs, such etretinate, tar, coal tar, anti pruritic and keratoplastic agents, such as cade oil, keratolytic agents, such as salicylic acid, emollients, lubricants, antiseptics and disinfectants, such as the germicide dithranol (also known as anthralin) photosensitizers, such as psoralen and methoxsalen and UV irradiation. Other agents may also be added, such as antimicrobial agents, antifungal agents, antibiotics and anti-inflammatory agents. Treatment by oxygenation (high oxygen pressure) may also be co-employed.

The topical compositions of the present invention may also be delivered to the skin using conventional dermal-type patches or articles, wherein the active ingredients composition is contained within a laminated structure, that serves as a drug delivery device to be affixed to the skin. In such a structure, the active ingredients composition is contained in a layer, or "reservoir", underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during active ingredients delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular active ingredients, vehicle, etc., i.e., the adhesive must be compatible with all components of the active ingredients-containing composition. Alternatively, the active ingredients-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active ingredients and to any other components of the active ingredients-containing composition, thus preventing loss of any components through the upper surface of the device. The backing layer may be either occlusive or nonocclusive, depending on whether it is desired that the skin become hydrated during active ingredients delivery. The backing is preferably made of a sheet or film of a preferably flexible elastomeric material. Examples of polymers that are suitable for the backing layer include polyethylene, polypropylene, and polyesters.

During storage and prior to use, the laminated structure includes a release liner. Immediately prior to use, this layer is removed from the device to expose the basal surface thereof, either the active ingredients reservoir or a separate contact adhesive layer, so that the system may be affixed to the skin. The release liner should be made from an active ingredients/vehicle impermeable material.

Such devices may be fabricated using conventional techniques, known in the art, for example by casting a fluid admixture of adhesive, active ingredients and vehicle onto the backing layer, followed by lamination of the release liner. Similarly, the adhesive mixture may be cast onto the release liner, followed by lamination of the backing layer. Alternatively, the active ingredients reservoir may be prepared in the absence of active ingredients or excipient, and then loaded by "soaking" in an active ingredients/vehicle mixture.

As with the topical formulations of the invention, the active ingredients composition contained within the active ingredients reservoirs of these laminated systems may contain a number of components. In some cases, the active ingredients may be delivered "neat," i.e., in the absence of additional liquid. In most cases, however, the active ingredients will be dissolved, dispersed or suspended in a suitable pharmaceutically acceptable vehicle, typically a solvent or gel. Other components, which may be present, include preservatives, stabilizers, surfactants, and the like.

The pharmaceutical compositions herein described may also comprise suitable solid or gel phase carriers or excipients. Examples of such carriers or excipients include, but are not limited to, calcium carbonate, calcium phosphate, various sugars, starches, cellulose derivatives, gelatin and polymers such as polyethylene glycols.

Dosing is dependent on the type, the severity and manifestation of the affliction and on the responsiveness of the subject to the active ingredients, as well as the dosage form employed, the potency of the particular conjugate and the route of administration utilized. Persons of ordinary skill in the art can easily determine optimum dosages, dosing methodologies and repetition rates. The exact formulation, route of administration and dosage can be chosen by the individual physician in view of the patient's condition. (See e.g., Fingl, et al., 1975, in "The Pharmacological Basis of Therapeutics", Ch. 1 p. 1).

Thus, depending on the severity and responsiveness of the condition to be treated, dosing can be a single or repetitive administration, with course of treatment lasting from several days to several weeks or until cure is effected or diminution of the skin lesion is achieved.

In some aspects the present invention utilizes in vivo and ex vivo (cellular) gene therapy techniques which involve cell transformation and gene knock-in type transformation. Gene therapy as used herein refers to the transfer of genetic material (e.g. DNA or RNA) of interest into a host to treat or prevent a genetic or acquired disease or condition or phenotype. The genetic material of interest encodes a product (e.g., a protein, polypeptide, peptide, functional RNA, antisense RNA) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved (1) ex vivo; and (ii) in vivo gene therapy. In ex vivo gene therapy cells are removed from a patient or are derived from another source, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ (Culver, 1998. (Abstract) Antisense DNA & RNA based therapeutics, February 1998, Coronado, Calif.). These genetically altered cells have been shown to express the transfected genetic material in situ.

The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore, as used herein the expression vehicle may, as needed, not include the 5'UTR and/or 3'UTR of the actual gene to be transferred and only include the specific amino acid coding region.

The expression vehicle can include a promoter for controlling transcription of the heterologous material and can be either a constitutive or inducible promoter to allow selective transcription. Enhancers that may be required to obtain necessary transcription levels can optionally be included. Enhancers are generally any nontranslated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., Molecular Cloning: A Laboratory Manual, Cold Springs Harbor Laboratory, New York 1989, 1992), in Ausubel et al., Current Protocols in Molecular Biology, John Wiley and Sons, Baltimore, Md. 1989), Chang et al., Somatic Gene Therapy, CRC Press, Ann Arbor, Mich. 1995), Vega et al., Gene Targeting, CRC Press, Ann Arbor Mich. (995), Vectors: A Survey of Molecular Cloning Vectors and Their Uses, Butterworths, Boston Mass. 1988) and Gilboa et al. (Biotechniques 4 (6): 504-512, 1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over is the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector introducing and expressing recombination sequences is the adenovirus-derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most tissues of epithelial origin as well as others. This vector as well as others that exhibit similar desired functions can be used to treat a mixed population of cells and can include, for example, in vitro or ex vivo culture of cells, a tissue or a human subject.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retroviruses, and is the process by which a single infected cell produces many progeny virions that bud off and infect neighboring cells. The result is that a large area becomes rapidly infected, most of which was not initially infected by the original viral particles. This is in contrast to vertical-types of infections, in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods and compositions of the invention will depend on desired cell type to be targeted and will be known to those skilled in the art.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment.

Procedures for in vivo and ex vivo cell transformation including homologous recombination employed in knock-in procedures are set forth in, for example, U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson, Methods in Enzymology, 194:251-270 1991); Capecchi, Science 244:1288-1292 1989); Davies et al., Nucleic Acids Research, 20 (11) 2693-2698 1992); Dickinson et al., Human Molecular Genetics, 2(8): 1299-1302 1993); Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742-750 1991); Jakobovits et al., Nature, 362:255-261 1993); Lamb et al., Nature Genetics, 5: 22-29 1993); Pearson and Choi, Proc. Natl. Acad. Sci. USA 1993). 90:10578-82; Rothstein, Methods in Enzymology, 194:281-301 1991); Schedl et al., Nature, 362: 258-261 1993); Strauss et al., Science, 259: 1904-1907 1993). Further, Patent Applications WO 94/23049, WO93/14200, WO 94/06908, WO 94/28123 also provide information.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Materials: Tissue culture media and serum were purchased from Biological Industries (Beit HaEmek, Israel). Enhanced Chemical Luminescence (ECL) was performed with a kit purchased from BioRad (Israel). Monoclonal anti p-tyr antibody was purchased from Upstate Biotechnology Inc. (Lake Placid, N.Y., USA). Polyclonal and monoclonal antibodies to PKC isoforms were purchased from Santa Cruz (Calif., USA) and Transduction Laboratories (Lexington, Ky.). The α6 rat antimouse mAb (GoH3) was purchased from Pharmingen (San Diego, Calif.). The antibody 6844 for the α6A cytoplasmic domain was a gift from Dr. V. Quaranta (Scripps Research Institute, La Jolla, Calif.). The rat mAb directed against the extracellular domain of mouse β4 (346-11A) was a gift from Dr. S. J. Kennel (Oak Ridge National Laboratory, Oak Ridge, Tenn.). Rat mAB to phosphotyrosine was purchased from Sigma (St. Louis, Mo.) and rabbit anti phosphoserine was purchased from Zymed (San Francisco, Calif.). Horseradish peroxidase-anti-rabbit and anti-mouse IgG were obtained from Bio-Rad (Israel). Leupeptin, aprotinin, PMSF, DTT, Na-orthovanadate, and pepstatin were purchased from Sigma Chemicals (St. Louis, Mo.). Insulin (humulinR-recombinant human insulin) was purchased from Eli Lilly France S A (Fergersheim, France). IGF1 was a gift from Cytolab (Israel).

Isolation and culture of murine keratinocytes: Primary keratinocytes were isolated from newborn skin as previously described (18). Keratinocytes were cultured in Eagle's Minimal Essential Medium (EMEM) containing 8% Chelex (Chelex-100, BioRad) treated fetal bovine serum. To maintain a proliferative basal cell phenotype, the final $Ca^{2+}$ concentration was adjusted to 0.05 mM. Experiments were performed five to seven days after plating.

Preparation of cell extracts and Western blot analysis: For crude membrane fractions, whole cell lysates were prepared by scraping cells into PBS containing 10 μg/ml aprotinin, 10 μg/ml leupeptin, 2 μg/ml pepstatin, 1 mM PMSF, 10 mM EDTA, 200 μM $NaVO_4$ and 10 mM NaF. After homogenization and 4 freeze/thaw cycles, lysates were spun down at 4° C. for 20 minutes in a microcentrifuge at maximal speed. The supernatant containing the soluble cytosol protein fraction was transferred to another tube. The pellet was resuspended in 250 μl PBS containing 1% Triton X-100 with protease and phosphatase inhibitors, incubated for 30 minutes at 4° C. and spun down in a microcentrifuge at maximal speed at 4° C. The supernatant contains the membrane fraction. Protein concentrations were measured using a modified Lowery assay (Bio-Rad DC Protein Assay Kit). Western blot analysis of cellular protein fractions was carried out as described (6).

Preparation of cell lysates for immunoprecipitation: Culture dishes containing keratinocytes were washed with $Ca^{2+}$/$Mg^{2+}$-free PBS. Cells were mechanically detached in RIPA buffer (50 mM Tris.HCl pH 7.4; 150 mM NaCl; 1 mM EDTA; 10 mM NaF; 1% Triton x100; 0.1% SDS, 1% Na deoxycholate) containing a cocktail of protease and phosphatase inhibitors (20 µg/ml leupeptin; 10 µg/ml aprotinin; 0.1 mM PMSF; 1 mM DTT; 200 µM orthovanadate; 2 µg/ml pepstatin). The preparation was centrifuged in a microcentrifuge at maximal speed for 20 minutes at 4° C. The supernatant was used for immunoprecipitation.

Immunoprecipitation: The lysate was precleared by mixing 300 µg of cell lysate with 25 µl of Protein A/G Sepharose (Santa Cruz, Calif., USA), and the suspension was rotated continuously for 30 minutes at 4° C. The preparation was then centrifuged at maximal speed at 4° C. for 10 minutes, and 30 µl of A/G Sepharose was added to the supernatant along with specific polyclonal or monoclonal antibodies to the individual antigens (dilution 1:100). The samples were rotated overnight at 4° C. The suspension was then centrifuged at maximal speed for 10 minutes at 4° C., and the pellet was washed with RIPA buffer. The suspension was again centrifuged at 15,000× g (4° C. for 10 minutes) and washed four times in TBST. Sample buffer (0.5 M Tris.HCl pH 6.8; 10% SDS; 10% glycerol; 4% 2-beta-mercaptoethanol; 0.05% bromophenol blue) was added and the samples were boiled for 5 minutes and then subjected to SDS-PAGE.

Attachment assays: Twenty four well petri plates (Greiner) were coated (250 µl/well) with 20 µg/ml of matrix proteins in PBS for 1 hour at 37° C. Following incubation, plates were washed and incubated with 0.1% BSA for 30 minutes at room temperature to block nonspecific binding. Keratinocyte cultures were trypsinized briefly with 0.25% trypsin and following detachment, cells were resuspended and keratinocytes ($1 \times 10^6$) added to the coated wells and incubated for 1 hour at 37° C. Nonadherent cells were removed, the wells were rinsed twice with PBS and the remaining cells were extracted in 1 M NaOH. Cell count was determined by protein concentrations using a modified Lowery assay (Bio-Rad DC Protein Assay Kit). Results were calculated by percentage relative to untreated controls.

Immunofluorescence: Primary keratinocytes were plated on laminin 5 coated glass slides. Two days old keratinocytes were infected with PKC adenovirus for one hour, washed twice with PBS and maintained in culture in low $Ca^{2+}$ EMEM. Twenty four hours post infection, cells were fixed in 4% paraformaldehyde for 30 minutes followed by permeabilization with 0.2% Triton for 5 minutes. For analysis, control and PKC infected keratinocytes were rinsed with PBS and incubated overnight at 4° C. with PKC antibodies (Santa Cruz) diluted in 1% BSA in PBS. After incubation, slides were washed twice for 10 minutes with PBS and incubated with biotinylated secondary anti rabbit antibody for 20 minutes, washed twice in PBS and incubated with Strepavidin-FITC for 20 minutes. For analysis of α6β4 staining, glass slides were treated with 0.2% triton X-100 for 5 minutes on ice followed by 5 minutes fixation in methanol. The slides were incubated with anti α6 or anti β4 antibodies overnight followed by incubation with biotinylated secondary anti rat antibody, respectively, for 20 minutes, washed twice in PBS and incubated with Strepavidin-FITC for 20 minutes. Following two washes in PBS, slides were mounted with glycerol buffer containing 1% of p-phenylenediamine (Sigma) and fluorescence examined by laser scanning confocal imaging microscopy (MRC1024, Bio-Rad, UK).

Adenovirus constructs: The recombinant adenovirus vectors were constructed as previously described (19). The dominant negative mutants of mouse PKCs were generated by substitution of the lysine residue at the ATP binding site with alanine. The mutant cDNA was cut from SRD expression vector with EcoR I and ligated into the pAxCA1w cosmid cassette to construct the Ax vector. The dominant negative activity of the genes was demonstrated by the abrogation of its autophosphorylation activity.

Transduction of keratinocytes with PKC isoform genes: The culture medium was aspirated and keratinocyte cultures were infected with the viral supernatant containing PKC recombinant adenoviruses for one hour. The cultures were then washed twice with MEM and re-fed. Ten hours post-infection cells were transferred to serum-free low $Ca^{2+}$-containing MEM for 24 hours. Keratinocytes from control and insulin-treated or IGF1-treated cultures were used for proliferation assays, $^{86}$Rb uptake, or extracted and fractionated into cytosol and membrane fractions for immunoprecipitation, immunofluorescence and Western blotting as described.

PKC activity: Specific PKC activity was determined in freshly prepared immunoprecipitates from keratinocyte cultures following appropriate treatments. These lysates were prepared in RIPA buffer without NaF. Activity was measured with the use of the SignaTECT Protein Kinase C Assay System (Promega, Madison, Wis., USA) according to the manufacturer's instructions. PKCα pseudosubstrate was used as the substrate in these studies.

Cell proliferation: Cell proliferation was measured by [$^3$H] thymidine incorporation in 24 well plates. Cells were pulsed with [$^3$H]thymidine (1 µCi/ml) overnight. After incubation, cells were washed five times with PBS and 5% TCA was added into each well for 30 minutes. The solution was removed and cells were solubilized in 1% Triton X-100. The labeled thymidine incorporated into cells was counted in a $^3$H-window of a Tricarb liquid scintillation counter.

$Na^+/K^+$ pump activity: $Na^+/K^+$ pump activity was determined by the measurements of ouabain-sensitive uptake of $^{86}$Rb by whole cells in 1 ml of $K^+$-free PBS containing 2 mM RbCl and 2.5 µCi of $^{86}$Rb. Rb uptake was terminated after 15 minutes by aspiration of the medium, after which the cells were rinsed rapidly four times in cold 4° C. $K^+$-free PBS and solubilized in 1% Triton X-100. The cells from the dish were added to 3 ml $H_2O$ in a scintillation vial. Samples were counted in a $^3$H-window of a Tricarb liquid scintillation counter. Rb-uptake specifically related to $Na^+/K^+$ pump activity was determined by subtraction of the cpm accumulated in the presence of $10^{-4}$ M ouabain from the uptake determined in the absence of the inhibitor.

PKC immunokinase assay: Purified and standardized PKC isozymes were kindly supplied by Dr. P. Blumberg (NCI, NIH, U.S.) and Dr. Marcello G. Kazanietz (University of Pennsylvania, School of Medicine). Primary keratinocytes were harvested in 500 µl 1% Triton Lysis Buffer (1% Triton-X 100, 10 µg/ml aprotinin and leupeptin, 2 µg/ml pepstatin, 1 mM PMSF, 1 mM EDTA, 200 FM $Na_2VO_4$, 10 mM NaF in 1× PBS). Lysates were incubated at 4° C. for 30 minutes, and spun at 16,000× g for 30 minutes at 4° C. Supernatants were transferred to a fresh tube. Immunoprecipitation of cell lysates was carried out overnight at 4° C. with 5 µg/sample anti-α6/GoH3 (PharMingen) and 30 µl/sample of protein A/G-Plus agarose slurry (Santa Cruz). Beads were washed once with RIPA buffer and twice with 50 mM Tris/HCl pH 7.5. 35 µl of reaction buffer (1 mM $CaCl_2$, 20 mM $MgCl_2$, 50 mM Tris.HCl pH 7.5) was added to each assay. To each assay, 5.5 μl/assay of a suspension of phospholipid vesicles containing either DMSO or 10 mM TPA was added to the slurry together with a standardized amount of specific PKC isozyme. The reaction was initiated by adding 10 μl/assay 125 mM ATP (1.25 μCi/assay [γ-32P] ATP, Amersham) and allowed to continue for 10 minutes at 30° C. The beads were then washed twice with RIPA buffer. 30 μl/sample protein loading dye (3× Laemmli, 5% SDS) was added and the samples were boiled for 5 minutes in a water bath. Proteins were separated by SDS-PAGE on a 8.5% gel, transferred onto Protran membranes (Schleicher & Schuell) and visualized by autoradiography. Phosphorylation of histones and phosphorylation of PKC substrate peptide were used as controls for PKC activity.

Experimental Results

Example 1

Effective Over-expression of PKC Isoforms Utilizing Recombinant Adenovirus Vectors By utilizing a recombinant β-galactosidase adenovirus a high infection rate was achieved with more then 90% of the cultured keratinocyte population expressing the recombinant protein. The recombinant β-galactosidase adenovirus infection did not affect cell viability or cell growth. Furthermore, β-galactosidase expression was sustained for up to two weeks of culture and was used as a control infection in following experiments. The efficiency of recombinant PKC adenovirus constructs to induce protein expression and be activated properly in mouse keratinocyte cultures was examined. As seen by Western blotting in FIG. 1, 24 hours following a 1 hour infection with recombinant PKC adenovirus constructs, a dramatic increase in specific PKC protein expression was observed five to ten fold above the endogenous expression levels of the specific isoforms. Recombinant protein could be detected in infected keratinocyte cultures as early as 6 hours following infection and peak expression was obtained by 24 hours. Protein expression was sustained throughout the culture period (up to fourteen days).

Example 2

Over-expressed PKC Isoforms are Activated by PKC Activators

Figure 2:
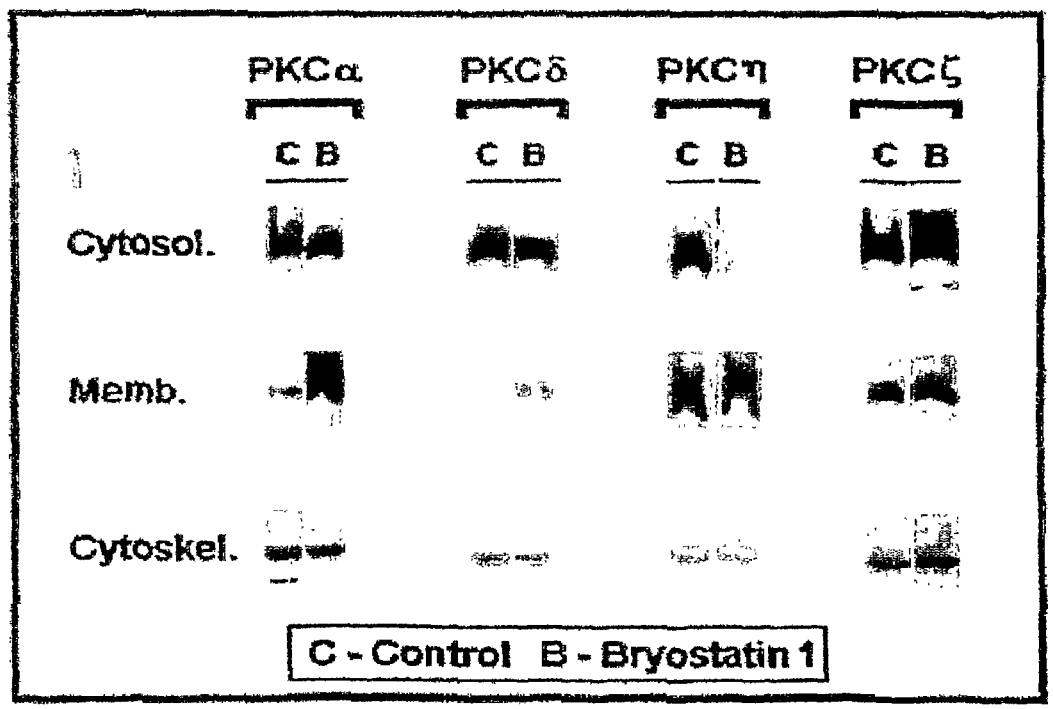
FIG. 2 shows that PKC activation by bryostatin 1 induces translocation of over-expressed PKC isoforms. Four day old primary keratinocytes were infected for 1 hour with isoform specific recombinant PKC adenoviruses. Twenty four hours following infection, cells were either untreated (C) or stimulated with bryostatin 1 (B) for 30 minutes, and fractionated. Protein samples were subjected to Western blotting and analyzed using isoform specific anti-PKC antibodies.

Recombinant proteins of the PKC isoforms responded typically to PKC activators. As seen in FIG. 2, treatment with bryostatin 1 induced translocation of PKCα and δ proteins to the membrane fraction, with a lesser effect on PKCη and ζ isoforms, similarly to results obtained with the endogenous isoforms and as expected from their cofactor requirements.

Example 3

Over-expressed PKC Isoforms are Active in Their Native Form

Figure 3:
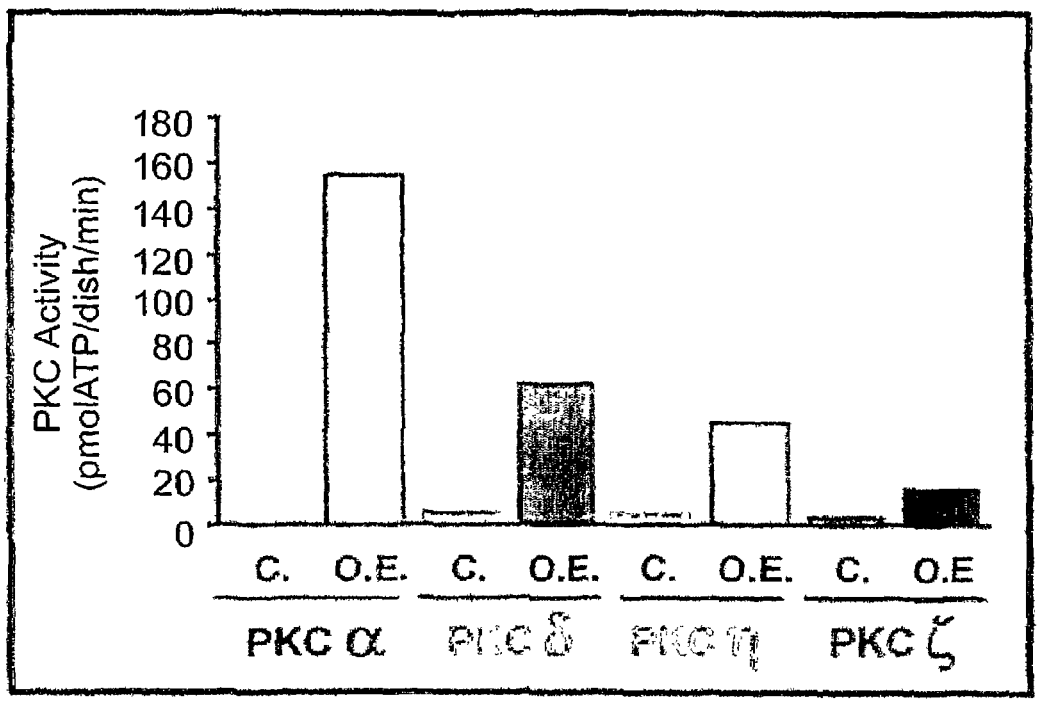
FIG. 3 shows that over-expressed PKC isoforms are active in their native form. Four days old primary keratinocytes were infected for 1 hour with isoform specific recombinant PKC adenoviruses. Eighteen hours following infection, cell lysates from uninfected control cells (C) and PKC isoforms over-expressing cells (OE) were immunoprecipitated using isoform specific anti-PKC antibodies. Immunoprecipitates were subjected to PKC activity assay as described in the Examples section that follows.

As early as 18 hours following infection, PKC kinase assays revealed that immunoprecipitates of distinct PKC isoforms were enzymatically active without further need of stimulation by PKC activators (FIG. 3).

Example 4

Figure 4:
FIG. 4 demonstrates that over-expression of specific PKC isoforms induces distinct morphologic changes in primary keratinocytes. Primary keratinocytes were either left untreated (C) or infected with recombinant PKC α, δ, η or ζ adenoviruses. Twenty four hours later, cultures were observed by bright field microscopy and photographed (×20).

Over-expression of Specific PKC Isoforms Induces Distinct Morphological Changes in Primary Keratinocytes Each of the PKC adenovirus constructs employed induced a specific morphological change in primary keratinocytes (FIG. 4). Uninfected primary mouse keratinocyte cultures and β-galactosidase infected cells presented a cubidal morphology typical to the proliferative basal cell characteristics in culture. Regardless of isoform specificity all PKC over-expressing keratinocytes showed morphological changes typical to PKC activation including cell elongation and the appearance of neuronal like projections. However, each one of the PKC isoforms had a characteristic effect on keratinocyte morphology. PKCα infection induced stratification of keratinocytes, with a typical flattened morphology. In contrast, PKCη appeared as condensed clones of cells, presenting morphological characteristics of basal cells proliferating at prompt rate (FIG. 4). Two of the isoforms appeared to effect cell matrix as well as cell-cell associations. 18-48 hours following PKCδ infection, cells appeared elongated and extended with neuronal like projections. This was followed by gradual cell loss off the culture dish which occurred progressively in the course of the culture period. Over-expressing PKCζ keratinocytes appeared as rounded keratinocyte clusters, which were attached loosely to the culture dish and were gradually lost several days following infection.

Example 5

Figure 5:
FIG. 5 shows distinct localization of over-expressed PKC isoforms in infected primary keratinocytes. Primary keratinocytes were plated on laminin 5-coated glass slides. Cultures were either untreated or infected with different recombinant PKC adenoviruses. Twenty four hours following infection, cells were fixed, washed and air-dried. Cultures were analyzed by immunofluorescence using isoform specific anti-PKC antibodies, followed by FITC conjugated secondary antibodies. Cells were scanned by confocal microscopy and representative fields were photographed.

Distinct Localization of Over-expressed PKC Isoforms in Infected Primary Keratinocytes The distinct morphological changes were associated with distinct cellular localization as characterized by immunofluorescence analysis. In proliferating keratinocytes, PKCα, PKCδ and PKCζ were expressed in the cytoplasm as well as in the plasma membrane. Similarly to endogenous protein expression, PKCη isoform was localized to the keratinocytes' perinuclear region (FIG. 5). A dynamic change in distribution was associated with PKCδ and PKCζ, where succeeding cell detachment PKC isoform expression was predominantly localized to the cell membrane (FIG. 5).

Example 6

Regulation of α6β4 Expression by PKC Isoforms Experimental Results

Figure 6:
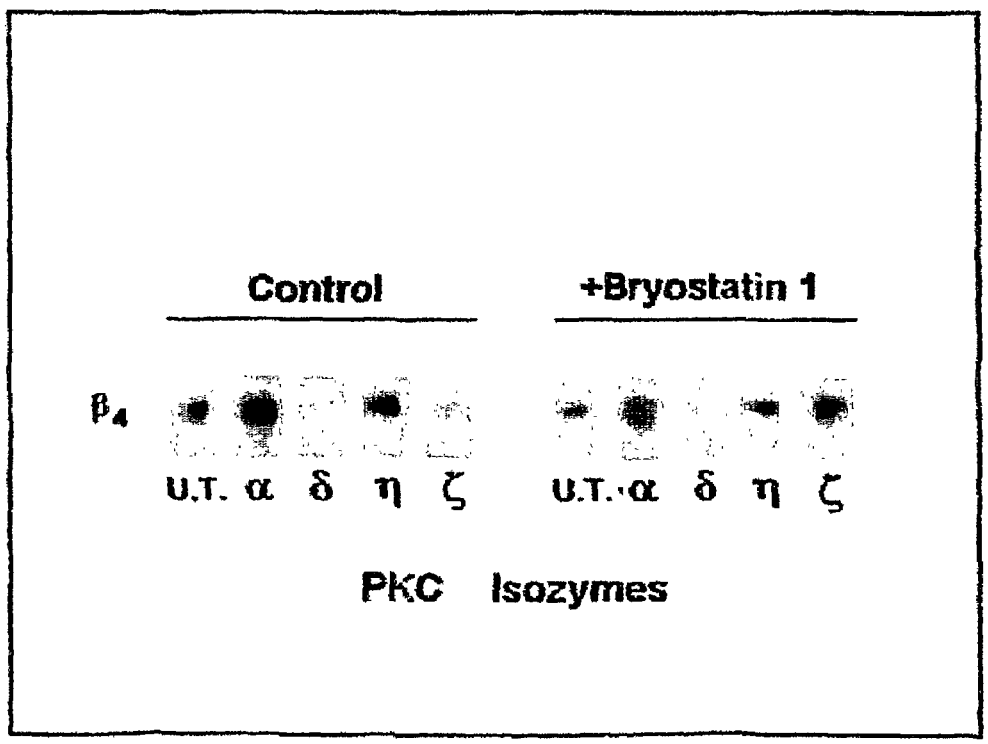
FIG. 6 demonstrates that PKC isoforms specifically regulate α6β4 integrin expression. Five days old primary mouse skin keratinocytes were untreated or infected with PKCα, PKCδ, PKCη or PKCζ recombinant adenoviruses. Forty eight hours post infection, membranal cell fractions were subjected to SDS-PAGE electrophoresis, transferred to nitrocellulose filters, immunoblotted with anti α6 and anti-β4 antibodies and analyzed by ECL.

The ability of specific PKC isoforms to regulate proteins which are characteristic of the basal phenotype of the proliferative basal layer was examined. As down regulation of α6β4 integrin is one of the early events taking place during keratinocyte differentiation, the ability of the various PKC isoforms to regulate expression of the α6β4 integrin, an integrin which is specifically localized to the hemidesmosomes of the basal layer was assessed. As can be seen in the immunoblot presented in FIG. 6, only PKCδ and PKCζ isoforms were able to down regulate α6β4 expression, in comparison to α6β4 integrin subunits levels in control keratinocytes. At the same time, α3 or β1 integrin subunits levels were not reduced. In contrast, consistently, over-expression of PKCα isoform resulted in increased α6β4 level two to three fold above control expression (FIG. 6). Over-expression of PKCη did not effect α6β4 protein expression. Several characteristics are associated with commitment of cells to differentiation and which follow the down regulation of the α6β4 protein including decrease in the proliferation rate, new keratin synthesis, cellular detachment and loss of attachment to basement membrane components. No changes in keratin expression were observed by over-expression of the different PKC isoforms. This included expression of K5 and K14, which are characteristic of the basal proliferating keratinocytes and K1 and K10, which are characteristic of the early stages of spinous differentiation. In addition, when proliferation rate was analyzed by $^3$H-thymidine incorporation there was no correlation between the loss of α6β4 expression and proliferation potential.

Example 7

Over-expressed PKCη and PKCδ Induce Keratinocytes Proliferation in Vitro

Figure 7:
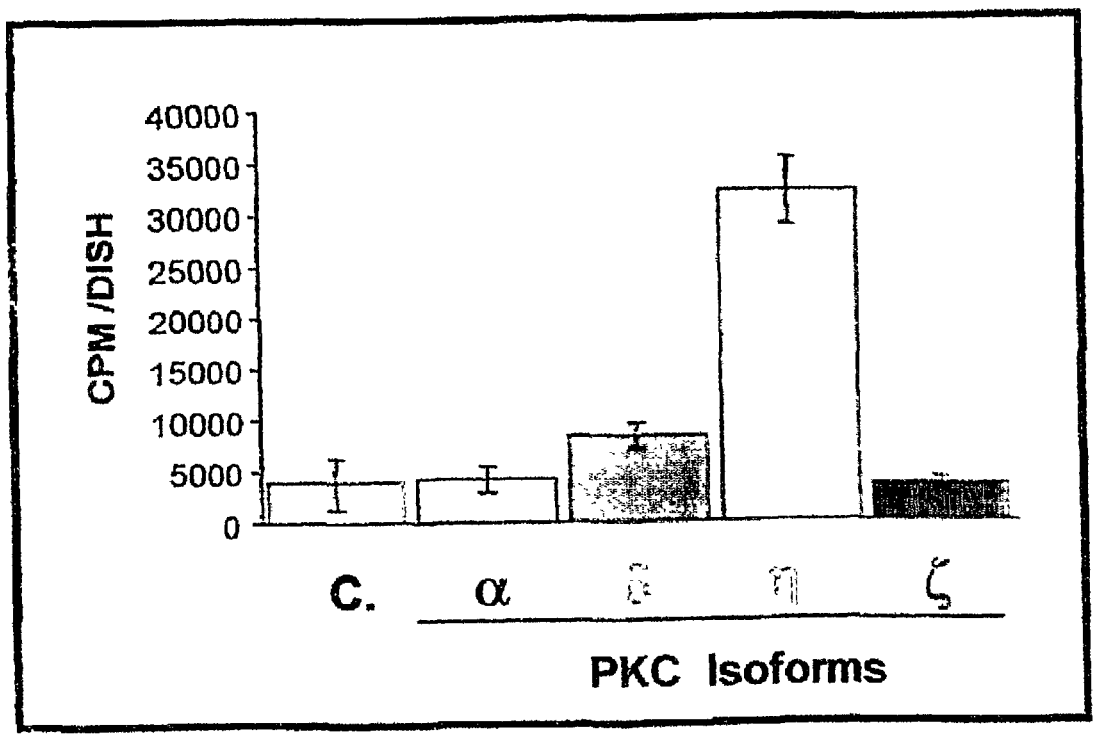
FIG. 7 shows that over-expression of PKCη and PKCδ induces keratinocyte proliferation. Five days old primary mouse skin keratinocytes were untreated or infected with PKCδ, PKCQα, PKCη or PKCζ recombinant adenoviruses. Forty eight hours post infection cell proliferation was analyzed by $^3$H-thymidine incorporation for 1 hour as described in experimental procedures. Results are presented as cpm/dish, in comparison to the β-galactosidase infected keratinocytes. Values are presented as mean±standard deviation of triplicate determinations in 3 separate experiments.

Over-expression of PKCη and PKCδ significantly induced keratinocyte proliferation five and two fold above control levels respectively (FIG. 7). PKCζ and PKCα did not affect cell proliferation.

Example 8

Over-expressed PKC δ and ζ Induce Keratinocytes Detachment in Vitro

The adhesion properties of PKCδ and ζ over-expressing keratinocytes was studied. In comparison to control keratinocytes no change in adhesion potential to specific matrix proteins including laminin1, laminin 5, fibronectin and collagen, was observed (data not presented). However, in cells over-expressing PKCδ and PKCζ isoforms, loss of cell contact with the culture dish was associated with gradual keratinocyte detachment from the culture dish (FIG. 4).

Example 9

Figure 8:
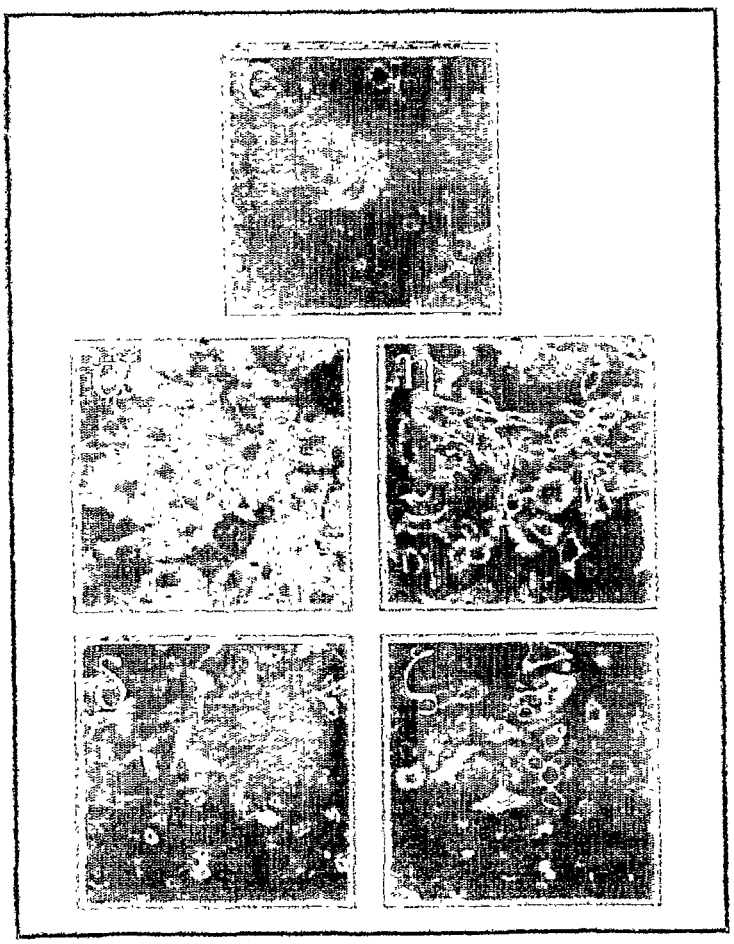
FIG. 8 demonstrates the PKC isoforms over-expression effects on hemidesmosomal localization of the α6β4 integrin. Primary keratinocytes were plated on laminin 5 coated glass slides and keratinocyte cultures were maintained in low $Ca^{2+}$ EMEM for 48 hours. Following that period of time, cultures were left untreated (A), or infected PKCα, PKCδ, PKCη or PKCζ recombinant adenoviruses (B-E, respectively). Twenty four hours post infection, keratinocytes were fixed with 4% paraformaldehyde followed by mild extraction with 0.2% Triton-X-100, washed in PBS and air dried as described in the experimental procedures. Cultures were subjected to immunofluorescence analysis utilizing isoform specific anti-α6 antibodies, followed by FITC conjugated secondary antibodies, as described in experimental procedures.
Figure 9A:
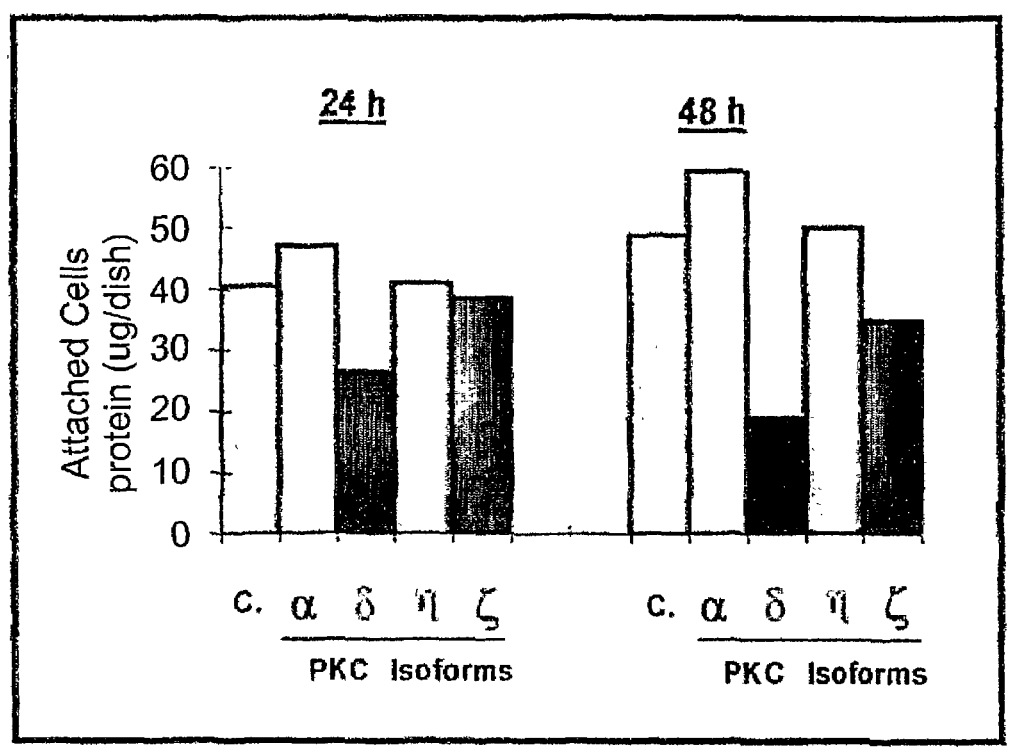
FIG. 9 shows that over-expressed PKCs δ and ζ induce keratinocyte detachment in vitro. (A)—Primary keratinocytes were either untreated (C) or infected with recombinant PKC α, δ, η or ζ adenoviruses. Cell attachment was analyzed 24 and 48 hours following infection, by lifting the cells and replating them on matrix coated dishes. Cell counts are presented as protein concentration (mg/dish) of the attached cells. (B)—Primary keratinocytes were either untreated (C) or infected with recombinant PKC α, δ, η or ζ adenoviruses. Cell detachment was analyzed 24 hours following infection, by collecting the detached floating cells in the culture medium. Cell counts are presented as protein concentration (mg/dish) of the detached cells.
Figure 9B:
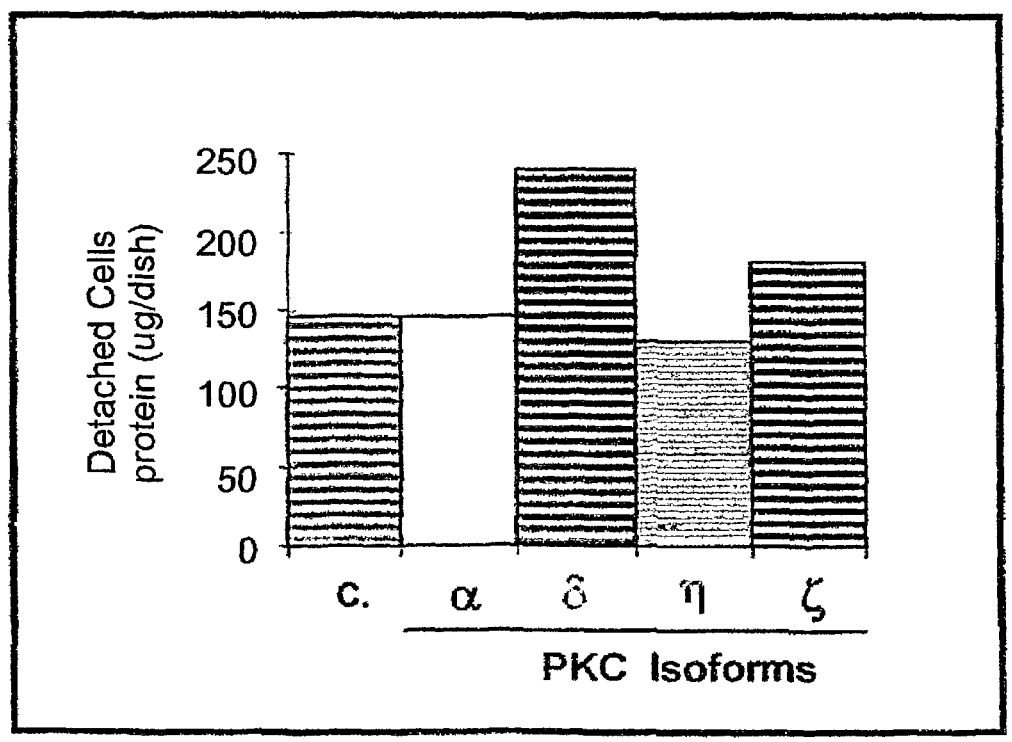

PKC Isoforms Over-expression Effects on Hemidesmosomal Localization of α6β4 Integrin As α6β4 expression is essential for the formation of the hemidesmosomal adhesion complex, the association of α6β4 down regulation and cell detachment with α6β4 localization to the hemidesmosome was examined. FIG. 8 presents immunofluorescent analysis of α6β4 association with the hemidesmosomal complexes. As seen in FIG. 8, in comparison to control infected keratinocytes, up regulation of α6β4 integrin expression in over-expressing PKCα keratinocytes (FIG. 6) is associated with increased integration of α6β4 to the hemidesmosomal complexes. Cells over-expressing PKCη also induced association of α6β4 integrin with the hemidesmosomal complexes, although less than observed in over-expressing PKCα cells. As expected, the significant down regulation of α6β4 integrin in PKCδ and PKCζ over-expressing keratinocytes was found to be associated with decreased integration of α6β4 with the cells' hemidesmosomal complexes (FIG. 8). These results suggest that α6β4 integrin plays an important role in cell-matrix association and keratinocytes encoring to the underlying basement membrane. Furthermore, PKCδ and ζ mediated α6β4 down regulation, initiate keratinocyte cell detachment in a pathway distinct from the keratinocyte differentiation processes. Finally, in order to link PKC mediated α6β4 down regulation, decrease hemidesmosomal α6β4 integration and specific morphological changes to keratinocyte detachment, the changes in the amount of attached and detached cells over-expressing the different PKC isoforms during the culture period were followed. In FIG. 9, attached cells were counted in cultures 24 and 48 hours following PKC adenoviral infection. As can be clearly observed, both PKCδ and PKCζ induced cell loss in vitro. In parallel, the loss of cells in culture was correlated with the increase in cells floating in the overlaying medium. These results indicate that PKCδ and PKCζ are important for control of the detachment step associated with the early stages of cell differentiation.

Example 10

Figure 10:
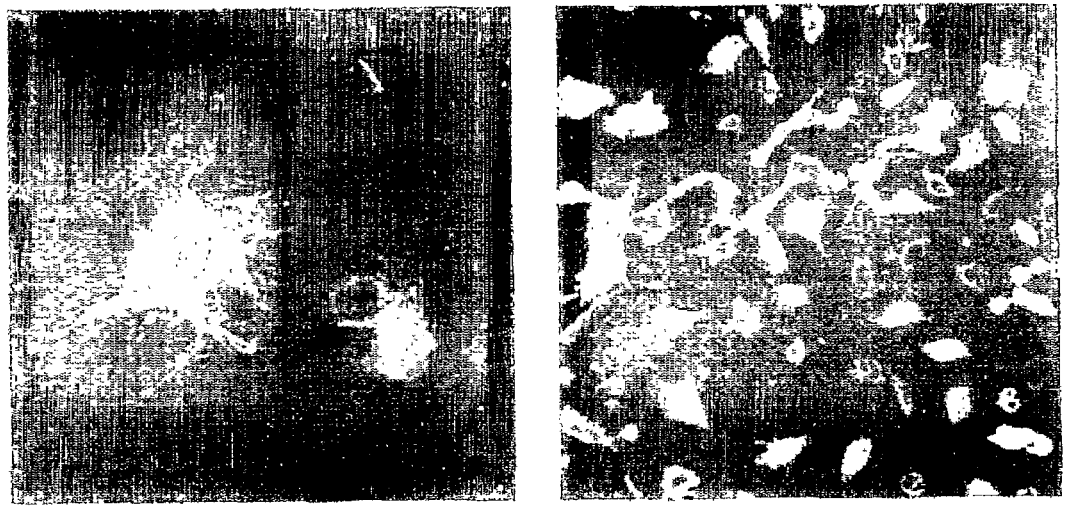
FIG. 10 demonstrates that PKCη is expressed in actively proliferating keratinocytes. Primary keratinocytes were plated on laminin 5-coated glass slides. Forty eight hours following plating keratinocytes were incubated with BrdU solution for 1 hour followed by immunofluorescence analysis using anti-PKCη (red) and anti BrdU (green) antibodies as described in the Examples section that follows. Cells were scanned by confocal microscopy and representative fields were photographed.
Figure 11:
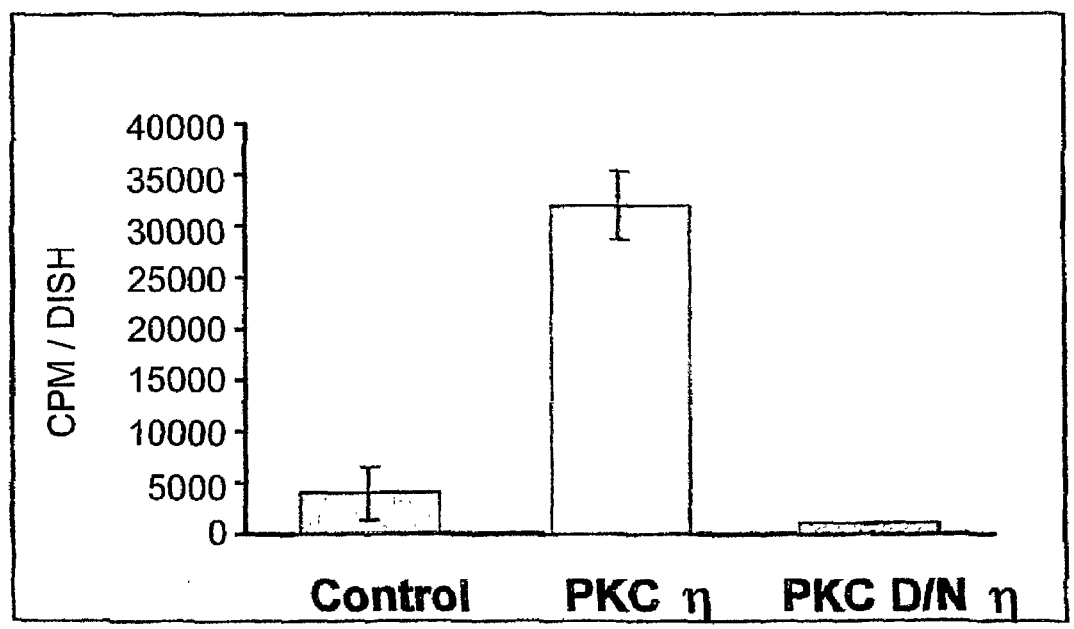
FIG. 11 demonstrates that PKCη induces, while PKC mutant reduces, keratinocyte proliferation. Primary skin keratinocytes were infected for 1 hour with recombinant PKCη or a dominant negative mutant of PKCη (DNPKCη or PKC DNη) adenoviruses. Forty eight hours post infection, cell proliferation was analyzed by 1-hour $^3$H-thymidine incorporation as described in the Examples section that follows. Results are presented as cpm/dish. Control-uninfected cells.

PKCη Differentially Regulate Keratinocyte Proliferation and Differentiation Under Physiological Settings As clearly shown in FIG. 7, cells over-expressing PKCη isoform proliferate at an accelerated rate, five to seven times above control uninfected cells, and consistently higher then keratinocyte cultures over-expressing other PKC isoforms. However, the induction of proliferation was dependent on the differentiation state of the keratinocytes as determined by regulating the Ca$^{2+}$ concentrations in the medium. In proliferating keratinocytes maintained under low Ca$^{2+}$ concentrations (0.05 mM) endogenous PKCη was localized to the perinuclear region of majority of the proliferating cells (FIG. 10). Under these conditions, PKCη over-expression induced a dramatic increase in keratinocyte proliferation (FIG. 11). However, when keratinocytes were differentiated by elevating the Ca$^{2+}$ concentrations to 0.12 mM, over-expression of PKCη did not induce proliferation but further stimulated keratinocyte differentiation. These results suggest that over-expressed PKCη induces proliferation only in physiologically proliferating cells but does not interfere with cellular differentiation. Divergence in regulation of PKCη expression was also seen in vivo. PKCη expression in actively proliferating skin as well as neuronal cells of the embryo was identified while in the mature adult brain no PKCη was observed and in the epidermis PKCη was localized to the granular layer in skin.

Example 11

Figure 12A:
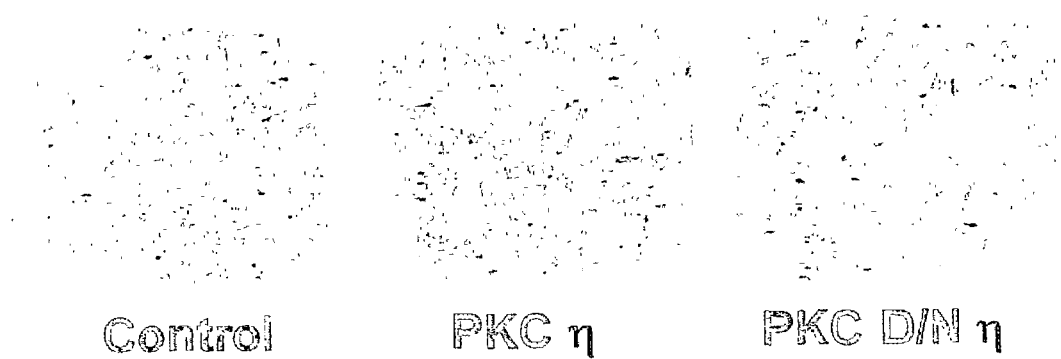
FIGS. 12A-B demonstrate that PKCη and DNPKCη over-expressions specifically regulate PKC localization and cellular morphology. Primary skin keratinocytes were infected for 1 hour with recombinant PKCη or a dominant negative mutant of PKCη (PKC DNη) adenoviruses. Forty eight hours post infection, keratinocytes were fixed and subjected to (A) bright field photography (×20) and (B) immunofluorescence analysis utilizing PKCη specific antibodies followed by FITC conjugated secondary antibodies as described in experimental procedures. Control-uninfected cells.
Figure 12B:
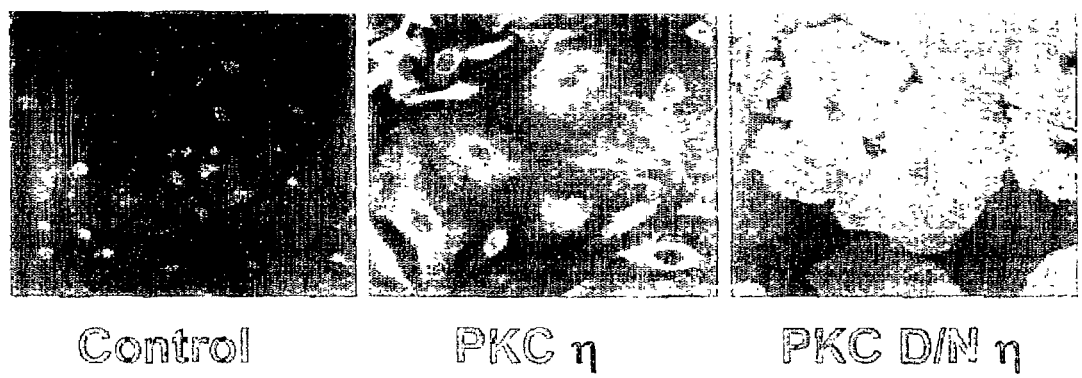
Figure 13A:
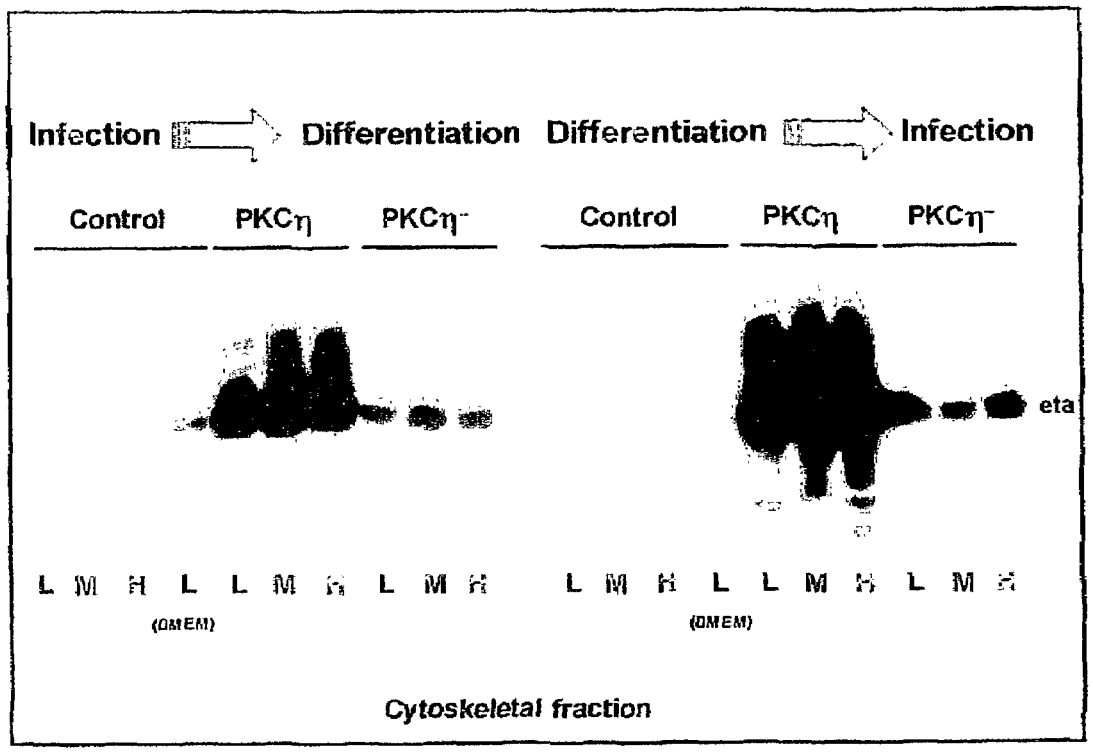
FIGS. 13A-B show that inhibition of PKCη expression induces keratinocyte differentiation in proliferating keratinocytes. Primary skin keratinocytes were either maintained proliferating in low $Ca^{2+}$ medium or differentiated in 0.12 mM $Ca^{2+}$ for 24 hours. Thereafter, keratinocytes were infected for 1 hour with recombinant PKCη or a dominant negative mutant of PKCη (PKC DNη) adenoviruses. Twenty four hours after infection, keratinocytes were either maintained in low $Ca^{2+}$ medium or transferred to differentiating medium containing 0.12 mM $Ca^{2+}$ for an additional 24 hours. Forty eight hours after infection, keratinocytes were extracted and subjected to SDS-PAGE gels. PKCη (A) and keratin 1 (B) expression was analyzed by Western blotting.
Figure 13B:
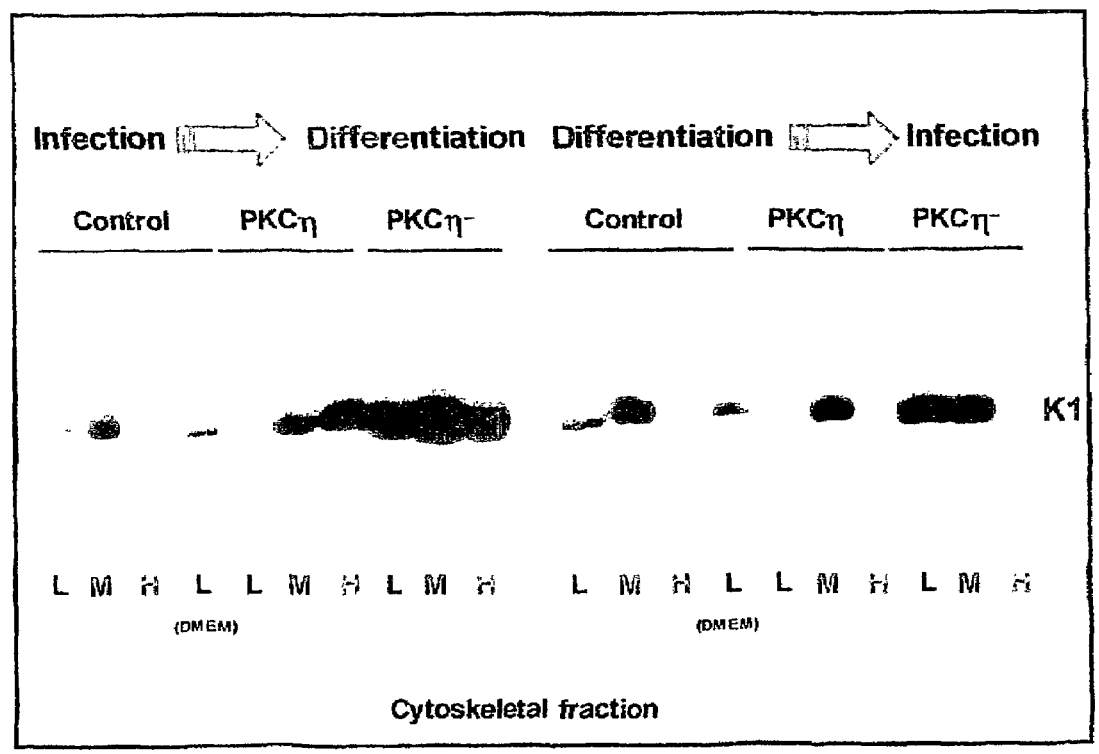

PKCη and DNPKCη Over-expression Specifically Regulates PKC Localization and Cellular Morphology To further corroborate the results which support a positive role for PKCη in both states of proliferation or differentiation in keratinocytes, the effects of a kinase inactive dominant negative adenovirus PKCη construct were analyzed by studying the effect of infection in proliferating and differentiating keratinocytes. As seen in FIG. 12 adenoviral infection of both PKCη and DNPKCη were efficient in both the proliferative and differentiative states. As predicted, in proliferating keratinocytes DNPKCη induced keratinocyte differentiation with a dramatic change in cell morphology including flattening of the cells, loss of cell-cell boundaries similarly to the morphological changes associated with Ca$^{2+}$ induced differentiation (FIGS. 12A-B). Furthermore, these changes were associated with shut off of keratinocyte proliferation (FIG. 11) and a dramatic 54 induction of differentiation markers including keratin 1, keratin 10, loricrin and Filagrin, which were elevated to similar levels presented in normal skin in vivo (FIGS. 13A-B). At the same time, upon initiation of the differentiation program, over-expression of DNPKCη did not abrogate Ca$^{2+}$ induced differentiation. These results suggest that PKCη and DNPKCη can be used for differentially regulating keratinocyte proliferation and differentiation under physiological settings.

Example 12

In vivo Experiments

Figure 14:
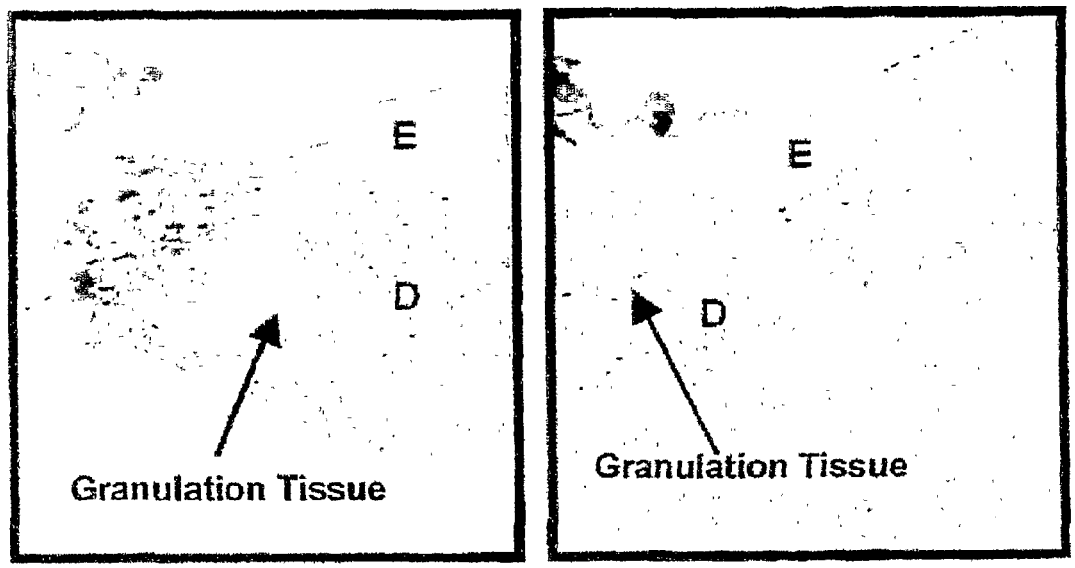
FIG. 14 demonstrates that topical in vivo expression of PKCη enhances the formation of granulation tissue and accelerates wound healing in mice incisional wounds. Whole skin 7 mm incisions were created on the back of nude mice. Topical application of control β-gal, PKCη and PKCα adenovirus suspension was applied at 1 d and 4 d following wounding. Whole skin wounds were fixed in 4% paraformaldehyde and skin sections were analyzed histologically by H&E staining and bright field microscopy. E—epidermis, D—dermis.

In order to test the ability of PKCη to differentially regulate cell proliferation and differentiation in vivo, the ability of PKCη to induce healing of full incisional wounds created on the back of nude mice was assessed. The ability of the keratinocytes to express the exogenous recombinant protein was verified by utilizing a control β-gal adenovirus. As can be seen in FIG. 14, two weeks after infection, β-gal expression is maintained in vitro keratinocytes as well as in vivo skin. Interestingly, when the wound healing process was examined in mice after local infection with control, PKCα and PKCη adenovirus constructs, only PKCη induced the formation of granulation tissue as early as four days following topical infection. This included also the organized formation of muscle, fat and dermal layers. At the same time in control and PKCα infected skins, condensed granulation tissue was not noticed and no closure of the wound was observed (FIG. 14). Therefore, PKCη can be considered as a primary candidate in regulating proliferation and differentiation of skin in the induction of wound healing processes.

Example 13

Figure 15:
FIG. 15 demonstrates that insulin, but not IGF1 specifically induces translocation of PKCδ in proliferating keratinocytes. Primary keratinocytes were isolated and plated as described in the Examples section that follows. Proliferating keratinocytes were maintained for five days in low $Ca^{2+}$ medium (0.05 mM) until they reached 80% confluency. Cells were stimulated with $10^{-7}$ M insulin (Ins) or $10^{-8}$ M IGF1 (IGF) for 15 minutes. Cells were lysed, as described, and 20 μg of membrane or cytosol extracts of stimulated and control unstimulated (Cont) cells were subjected to SDS-PAGE and transfer. Blots were probed with specific polyclonal antibodies to each PKC isoform.
Figure 15:
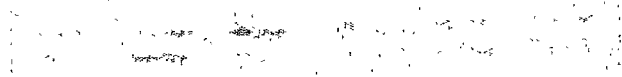
Figure 15:
Figure 15:
Figure 15:

Insulin Specifically Induces Translocation of PKCδ in Proliferating Keratinocytes Two PKC isoforms expressed in skin were found to affect keratinocyte proliferation: PKCη and PKCδ. In order to try and identify the endogenous factors, which activate specific PKC isoforms regulating skin proliferation, the ability of several growth factors which are known to promote keratinocyte proliferation including: EGF, KGF, insulin, PDGF and IGF1 to activate specific PKC isoforms in a growth dependent manner was assessed. PKC isoforms α, δ, ε, η and ζ are expressed in the skin. As activation of PKC isoforms is associated with their translocation to membrane fractions, the effects of these growth factors on the translocation of the various PKC isoforms from cytosol to the membrane were examined. As seen in FIG. 15, as early as 5 minutes following stimulation, insulin specifically induced translocation of PKCδ from the cytoplasm to the membranal fractions. Membrane expression of PKCδ was maintained for several hours following insulin stimulation. In contrast, IGF1 reduced PKCδ expression in the membrane and increased its relative level of expression in the cytoplasm fraction. No other growth factor significantly affected PKCδ translocation and localization. No change in distribution of the other PKC isoforms was seen following stimulation by any of the growth factors including IGF1 and insulin.

Example 14

Insulin Specifically Induces Activation of PKCδ in Proliferating Keratinocytes

Figure 16:
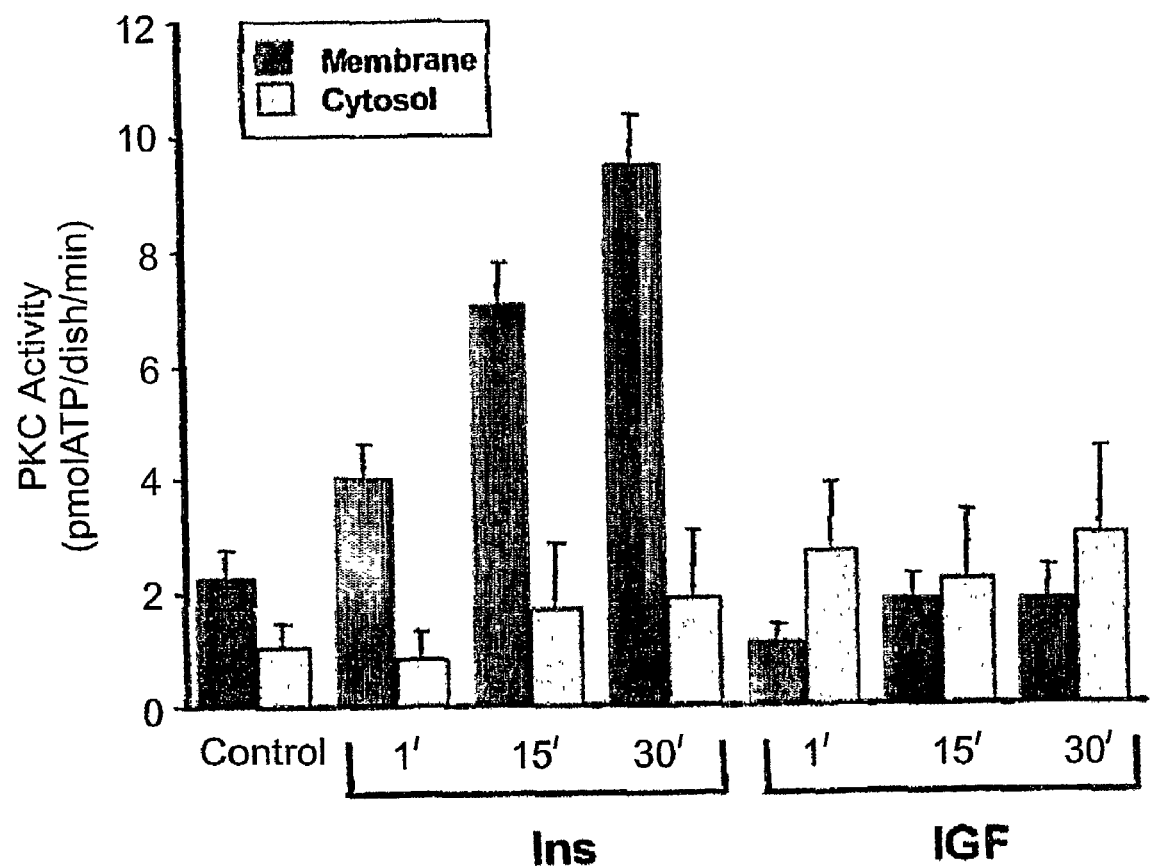
FIG. 16 shows that insulin but not IGF1 induces PKCδ activity. To determine PKCδ activity, five-day keratinocyte cultures were stimulated with $10^{-7}$ M insulin (Ins) or $10^{-8}$ M IGF1 (IGF) for the designated times (1, 15, or 30 minutes). PKCδ was immunoprecipitated from membrane (blue bars, mem) and cytosol (purple bars, cyto) fractions using specific anti-PKCδ antibody. PKCδ immunoprecipitates were analyzed for PKC activity utilizing an in vitro kinase assay as described in experimental procedures. Each bar represents the mean±SE of 3 determinations in 3 separate experiments. Values are expressed as pmol ATP/dish/min.

In order to determine whether the translocation of PKCδ is sufficient for activation, kinase activity of PKC immunoprecipitates from the cytoplasm and membrane fractions of insulin and IGF1 treated keratinocytes was measured. As shown in FIG. 16, insulin but not IGF1 increased activity of PKCδ in the membrane fraction. No elevation in PKCα activity was observed in the cytoplasm fraction. The insulin-induced activation was specific for PKCδ and no activation of PKCs α, ε, η, or ζ was observed for up to 30 minutes following insulin stimulation. Altogether, these results suggest selective stimulation by insulin but not IGF1 of PKCδ activation.

Example 15

Insulin and IGF1 Have an Additive Effect on Keratinocyte Proliferation

Figure 17A:
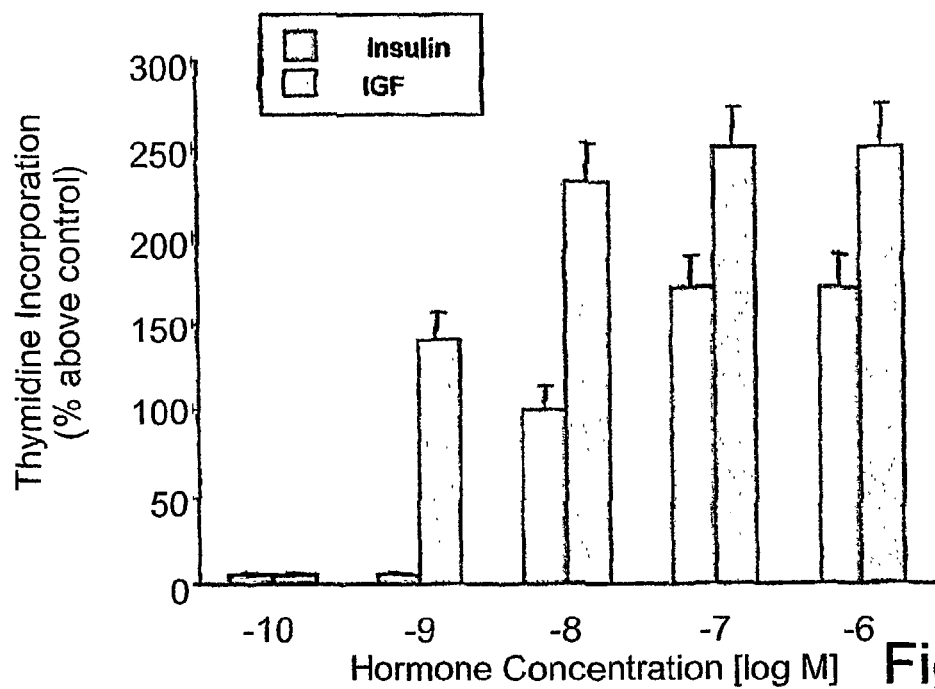
FIGS. 17A-B show that insulin and IGF1 have an additive effect on keratinocyte proliferation. Proliferating keratinocytes were maintained for five days in low $Ca^{2+}$ medium (0.05 mM) until they reached 80% confluence. (A) is Five-day keratinocyte cultures were stimulated for 24 hours with insulin or IGF1 at the designated concentrations. (B) In parallel, keratinocytes were stimulated with $10^{-7}$ M insulin (Ins) and increasing doses of IGF1 (IGF). At each concentration the right column (striped bar) represents proliferation observed when both hormones were added together. The left bar demonstrates the separate effect of $10^{-7}$ M insulin (red bars) and increasing concentrations of IGF1 (gray bars). Thymidine incorporation was measured as described in experimental procedures. The results shown are representative of 6 experiments. Each bar represents the mean±SE of 3 determinations expressed as percent above control unstimulated keratinocytes.
Figure 17B:
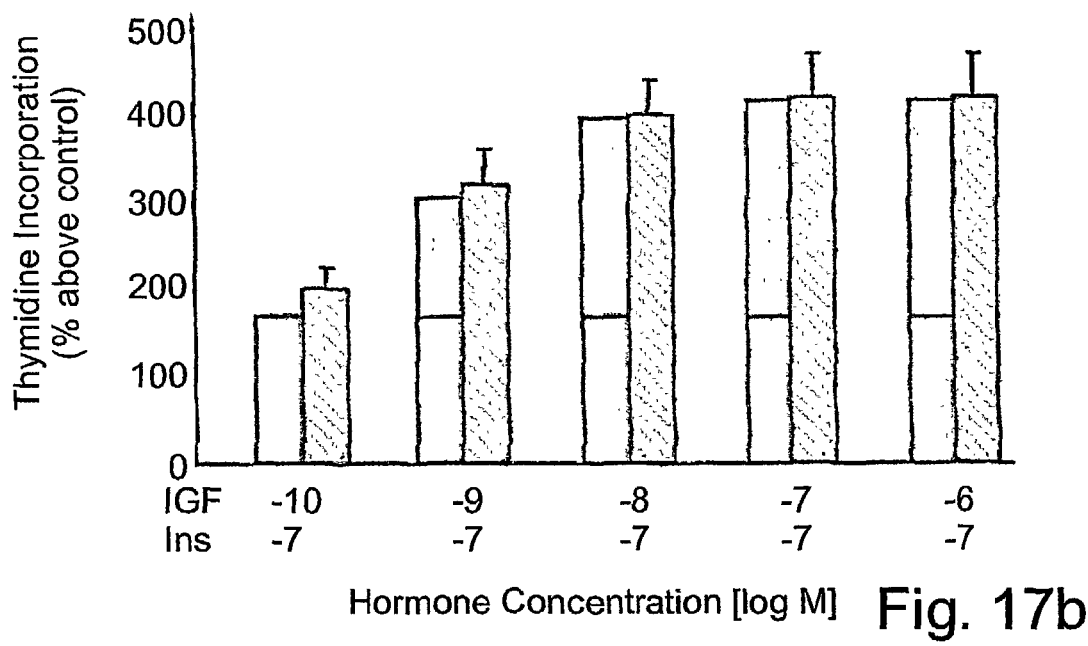

In order to analyze if the specific activation of PKCδ signifies specific insulin induced mitogenic pathway in keratinocytes the mitogenic effects of both insulin and IGF1 were examined by studying their ability to induce keratinocyte proliferation as measured by thymidine incorporation. As shown in FIG. 17A, both insulin and IGF1 stimulated thymidine incorporation in a dose dependent manner with maximal induction achieved at $10^{-7}$ and $10^{-8}$ M, respectively. At each concentration, the maximal stimulation by IGF1 was greater than that by insulin. Interestingly, at all concentrations, when both hormones were given together, the mitogenic effects were additive (FIG. 17B). These results suggest that insulin regulates keratinocyte proliferation through a distinct pathway independent of IGF1 induced keratinocyte proliferation.

Example 16

Figure 18A:
FIGS. 18A-B demonstrate the over-expression of recombinant PKC adenovirus constructs. Keratinocyte cultures were infected utilizing recombinant adenovirus constructs containing wild type PKCδ (WTPKCδ), wild type PKCα (WTPKCα), or a dominant negative PKCδ mutant (DNPKCδ). (A) Following infection, cells were cultured for 24 hours, harvested, and 20 μg of protein extracts were analyzed by Western blotting using specific anti PKCα or anti PKCδ antibodies. The blots presented are representative of 5 separate experiments. (B) Twenty four hours following infection, cells were harvested and PKCα or PKCδ immunoprecipitates were evaluated by in vitro kinase assay.
Figure 18A:
Figure 18B:
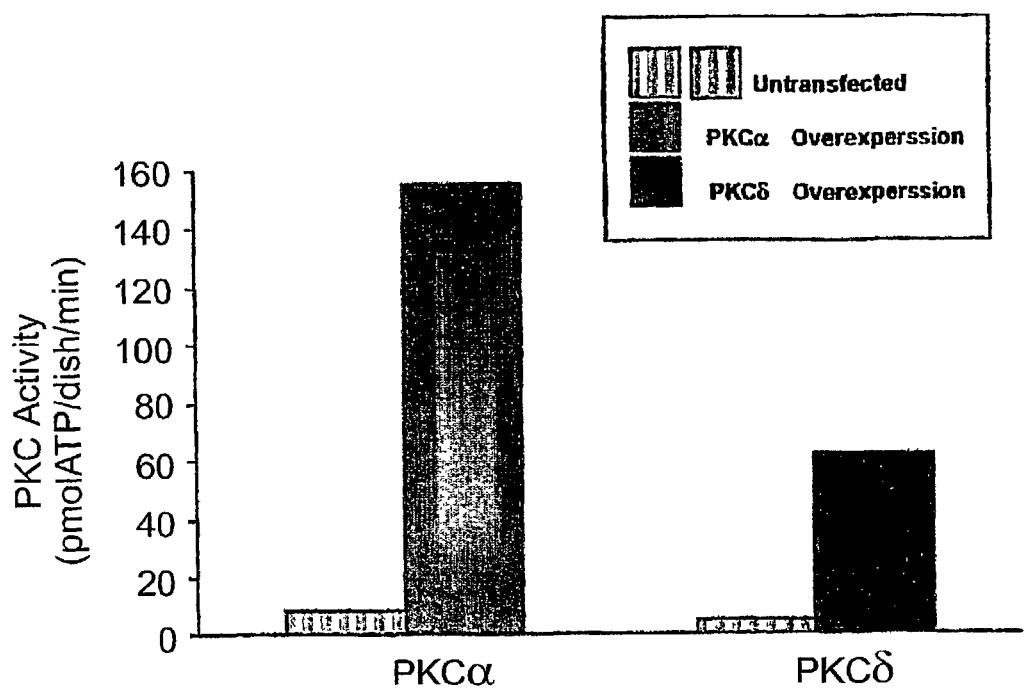
Figure 19:
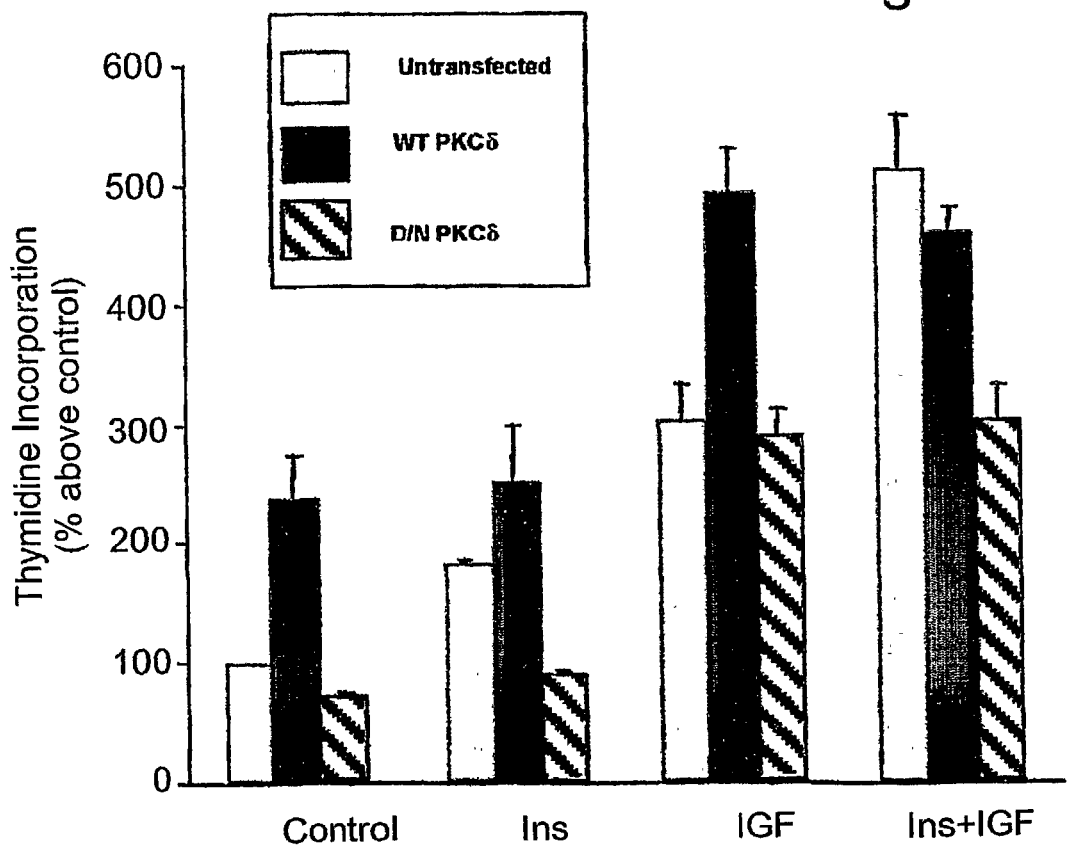
FIG. 19 shows the effects of PKC over-expression on insulin or IGF1—induced proliferation. Non-infected (light blue bars), or cells over-expressing WTPKCδ (dark blue bars) or DNPKCδ (slashed blue bars) were treated for 24 hours with $10^{-7}$ M insulin (Ins), $10^{-8}$ M IGF1 (IGF) or both (Ins+IGF). Thymidine incorporation was measured as described in experimental procedures. Each bar represents the mean±SE of 3 determinations in 3 experiments done on separate cultures. Values are expressed as percent of control, unstimulated cells from the same culture in each experiment.

The Association Between Insulin-induced PKC δ Activation and Insulin-induced Keratinocyte Proliferation In order to directly study the association between insulin-induced PKCδ activation and insulin-induced keratinocyte proliferation, recombinant PKC adenovirus constructs were used to over-express both wild type PKCδ (WTPKCδ) as well as a kinase-inactive dominant negative mutant of PKC, which abrogates the endogenous PKCδ activity (DNPKCδ). The effects of over-expression of WTPKCδ and DNPKCδ on insulin-induced keratinocyte proliferation were examined. Both constructs, as well as a PKCα construct, were efficiently expressed in keratinocytes (FIG. 18A). Furthermore, infection with PKCδ and PKCα induced isoform-specific PKC activity several fold above control levels (FIG. 18B). As expected, over-expression of DNPKCδ did not induce PKC activity. As can be seen in FIG. 19A, insulin treatment of untransfected cells or over-expression of WTPKCδ without insulin treatment, increased thymidine incorporation to approximately identical levels, two to three fold over untreated cells, or cells transduced with PKCα. Moreover, addition of insulin to cells already over-expressing WTPKCδ did not cause any additional increase in thymidine incorporation. IGF1 increased thymidine uptake similarly in both non-infected cells and in cells over-expressing WTPKCδ and PKCα (FIG. 19A). The direct involvement of PKCδ in insulin induced proliferation was further proven by abrogating PKCδ activity. As seen in FIG. 19B, basal thymidine incorporation in cells over-expressing the dominant negative PKCδ was slightly, but significantly, lower than that in non-infected cells. Over-expression of DNPKCδ completely eliminated insulin-induced proliferation but did not affect IGF1-induced proliferation. Moreover, the additive effects of insulin and IGF1 was reduced to that of IGF1 alone.

Example 17

Specificity of PKCδ Activation to the Insulin-mediated Pathway

Figure 20:
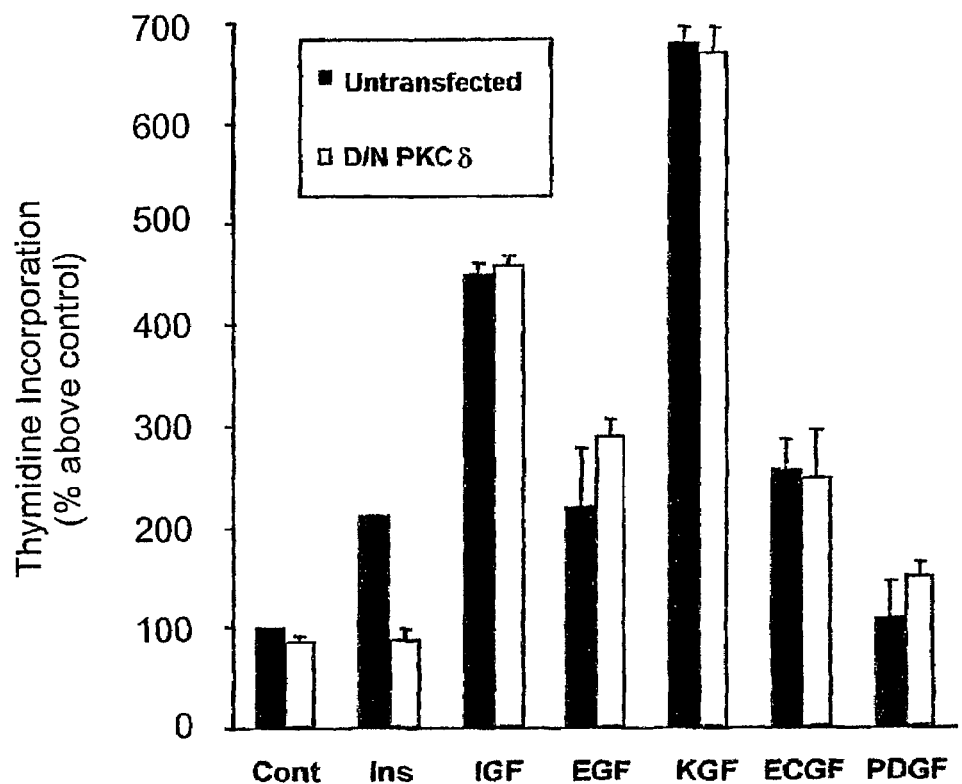
FIG. 20 shows that inhibition of PKCδ activity specifically abrogates insulin induced keratinocyte proliferation. Primary keratinocytes were cultured as described in the Examples section that follows. Non-infected cells or keratinocytes infected with DNPKCδ were stimulated for 24 hours with the following growth factor concentrations: $10^{-7}$ M insulin (Ins), $10^{-8}$ M IGF1 (IGF), 10 ng/ml EGF, 10 ng/ml PDGF, 1 ng/ml KGF or 5 ng/ml ECGF. Thymidine incorporation was measured as described in the Examples section that follows. Each bar represents the mean±SE of 3 determinations in 3 experiments done on separate cultures. Values are expressed as percent of control, unstimulated cells from the same culture in each experiment.
Figure 21:
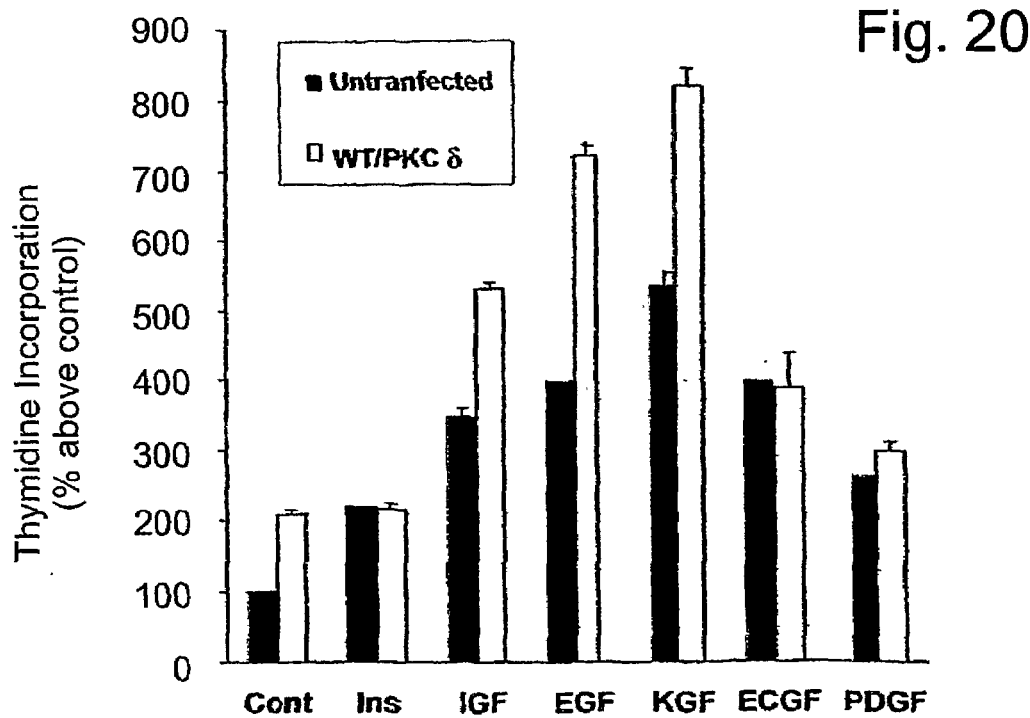
FIG. 21 shows that over-expression of PKCδ mediates specifically insulin induced keratinocyte proliferation. Primary keratinocytes were cultured as described under FIG. 1. Non-infected cells or keratinocytes infected with over-expressed WTPKCδ were stimulated for 24 hours with the following growth factor concentrations: $10^{-7}$ M insulin (Ins), $10^{-7}$ M IGF1 (IGF), 10 ng/ml EGF, 10 ng/ml PDGF, 1 ng/ml KGF or 5 ng/ml ECGF. Thymidine incorporation was measured as described in the Examples section that follows. Each bar represents the mean±SE of three determinations in three experiments done on separate cultures. Values are expressed as percent of control, unstimulated cells from the same culture in each experiment.

The specificity of PKCδ activation to the insulin-mediated pathway was analyzed by investigating the effects of PKCδ and DNPKCδ on the mitogenic response to a variety of growth factors including: IGF1, EGF, KGF, ECGF and PDGF. As seen in FIG. 20, the over-expression of DNPKCδ selectively eliminated the proliferative effects induced by insulin but did not block those of any of the other growth factors tested. However, the over-expression of PKCδ mimicked insulin induced proliferation and did not affect IGF1 induced proliferation. The proliferation induced by stimulation with EGF and KGF was increased (FIG. 21). These data indicate that PKCδ activation by insulin, mediates proliferation of keratinocytes through a pathway involving PKCδ and that this pathway is upstream of EGF and KGF signaling, two major growth factors known to regulate keratinocyte proliferation. Overall, insulin was found to be a specific regulator of PKCδ activity, which could be a specific candidate in regulating keratinocyte proliferation induced by insulin, EGF and KGF.

Example 18

Figure 23:
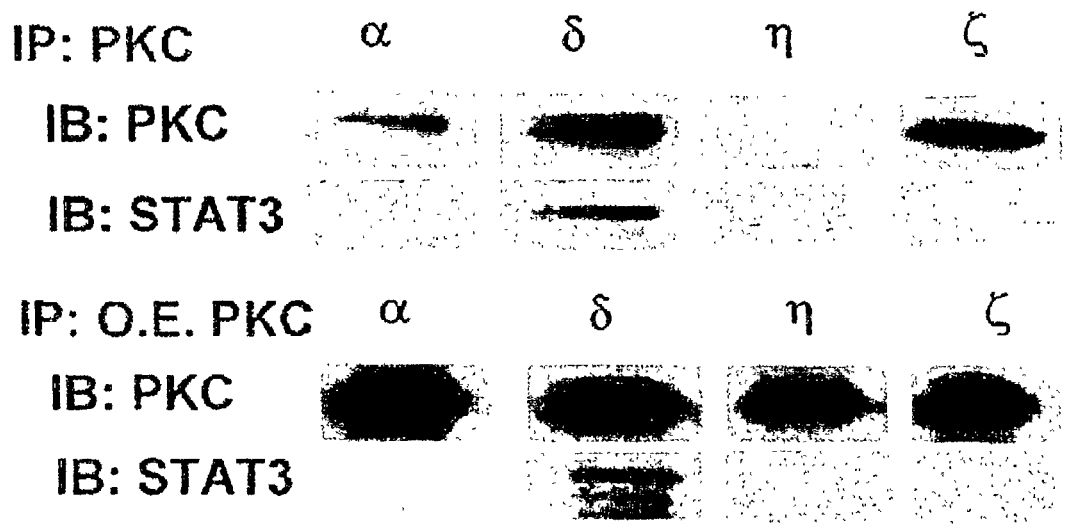
FIG. 23 identifies a specific interaction between STAT3 and PKCδ in primary skin keratinocytes. Primary keratinocytes were either untreated (upper panel) or infected for 1 hour with isoform specific, recombinant PKC adenoviruses (lower panel). Cells were extracted and immunoprecipitated (IP) with isoform specific PKC antibodies. The immunoprecipitates were subjected to Western blot analysis using anti-PKCs or anti-STAT3 antibodies.
Figure 24:
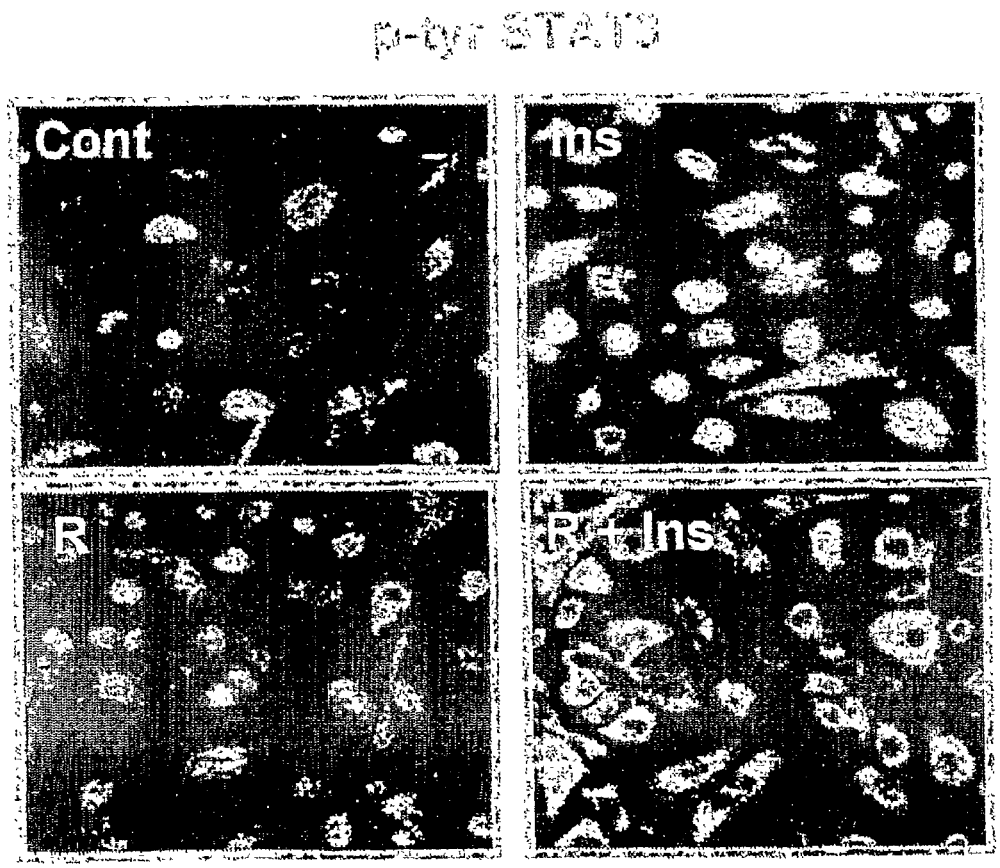
FIG. 24 demonstrates the importance of PKCδ activation to insulin induced transcriptional activation of STAT3. Primary keratinocytes were plated on glass slides and maintained for 5 days in low $Ca^{++}$ medium (0.05 mmol/l) until they reached 80% confluency. Cells were untreated (Cont, upper panel) or pre-treated with 5 μM Rottlerin for 7 minutes (R, lower panel), followed by $10^{-7}$ M insulin for 5 minutes (Ins). Cells were fixed by methanol, washed and air-dried. Cultures were analyzed by immunofluorescence using antiphospho-Tyr-705-STAT3 antibody, followed by FITC conjugated secondary antibody. Cells were scanned by confocal microscopy.
Figure 25:
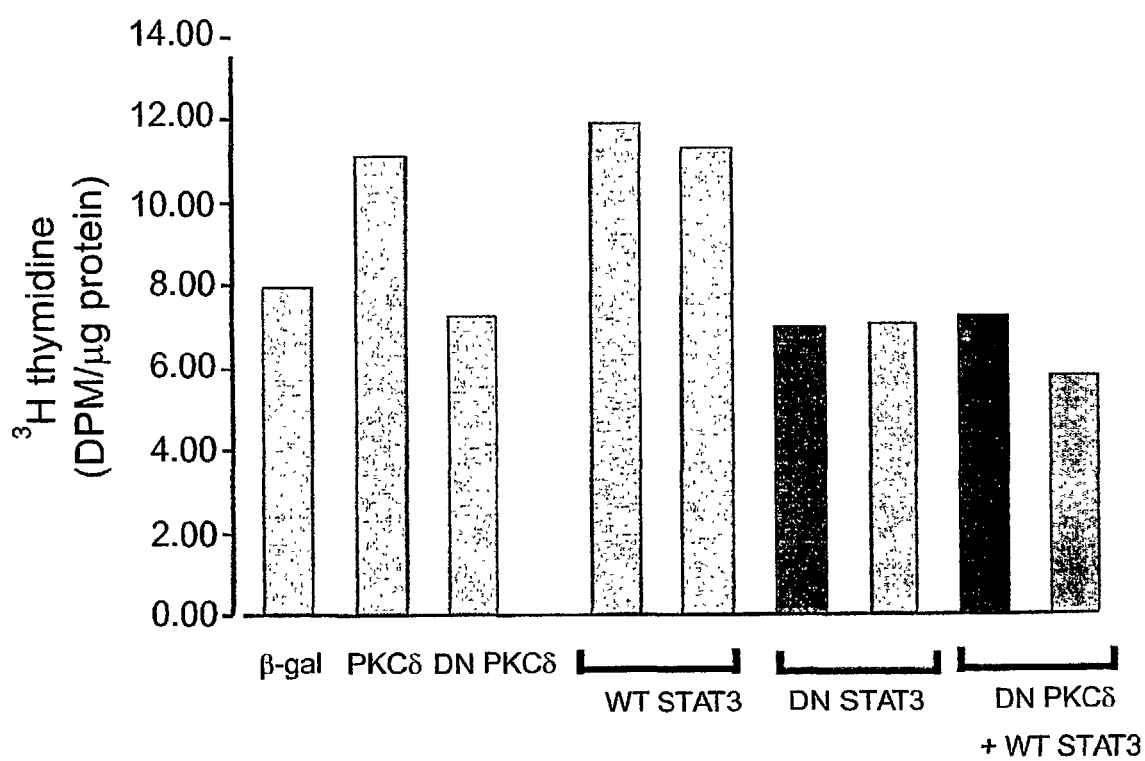
FIG. 25 demonstrates that overexpression of DN PKCδ inhibits keratinocyte proliferation induced by overexpression of PKCδ and STAT3. Primary keratinocytes were infected for 1 hour with recombinant adenovirus constructs containing β-Gal (for control), PKC α, WT STAT3, DN STAT3 or double-infected with DN PKCδ, followed by STAT3. 24 hours following infection, cell proliferation was analyzed by 1 hour $^3$H-thymidine incorporation. The results are presented as DPM/mg protein. Each bar represents the mean of three determinations in a plate from the same culture.

Insulin Induced PKCδ Activity and Keratinocyte Proliferation is Mediated by STAT3 Transcriptional Activation The role of PKCδ in insulin signaling was further characterized and found to involve induction of transcriptional activation mediated by STAT3. As senn in FIG. 23, in primary keratinocytes, PKCδ was shown to specifically associate with STAT3. Following insulin stimulation, PKCδ is activated and in turn phosphorylates and activates STAT3 (FIG. 24). Moreover, abrogating PKCδ activity by a pharmacological inhibitor (rottlerin) inhibits activaiton as well as nuclear translocation of STAT3. Furthermore, as seen in FIG. 25, overexpression of STAT3 induces a similar proliferation as that induced by insulin and by overexpression of PKCδ and abrogation of PKCδ activity by overexpression of a dominant negative PKCδ mutant abolishes the ability of STAT3 to induce keraitnocyte proliferation. Overall these results suggest that insulin and PKCδ play a role in transcriptional activation associated with keratinoycte proliferation.

Example 19

PKCδ and PKCζ are Essential to the Wound Healing Process in vivo

Figure 22A:
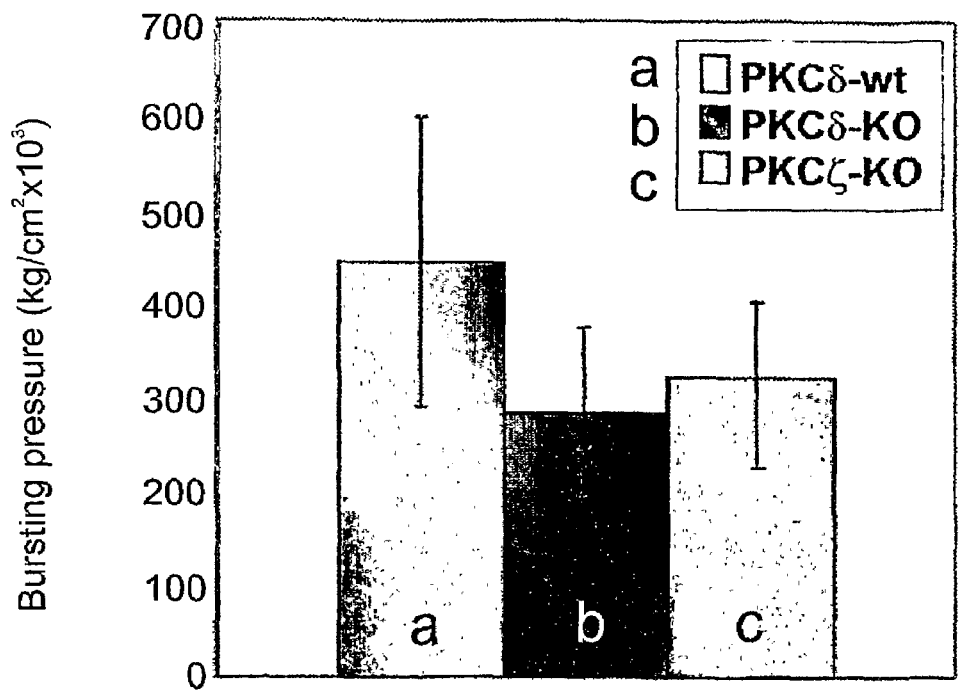
FIGS. 22A-B substantiate the significance of PKCδ and PKCζ in the wound healing process of skin in vivo. Utilizing in vivo mouse model of newly developed isoform specific PKC null mice, PKCα, PKCδ and PKCζ null mice and their wild type littermates were subjected to a wound healing study. Mice were anesthetized and a skin through punch biopsies of 4 mm in diameter were created on the mice back. After a week follow-up, mice skin was removed and skin wound healing was quantified by subjecting skin flaps to a wound strength test utilizing a bursting chamber technique. Values are expressed as bursting pressure which represents the maximal pressure within the chamber monitored until bursting occurs. Results represent determinations obtained in distinct groups of 12-20 mice. Experiments were repeated at least 3 times.
Figure 22B:
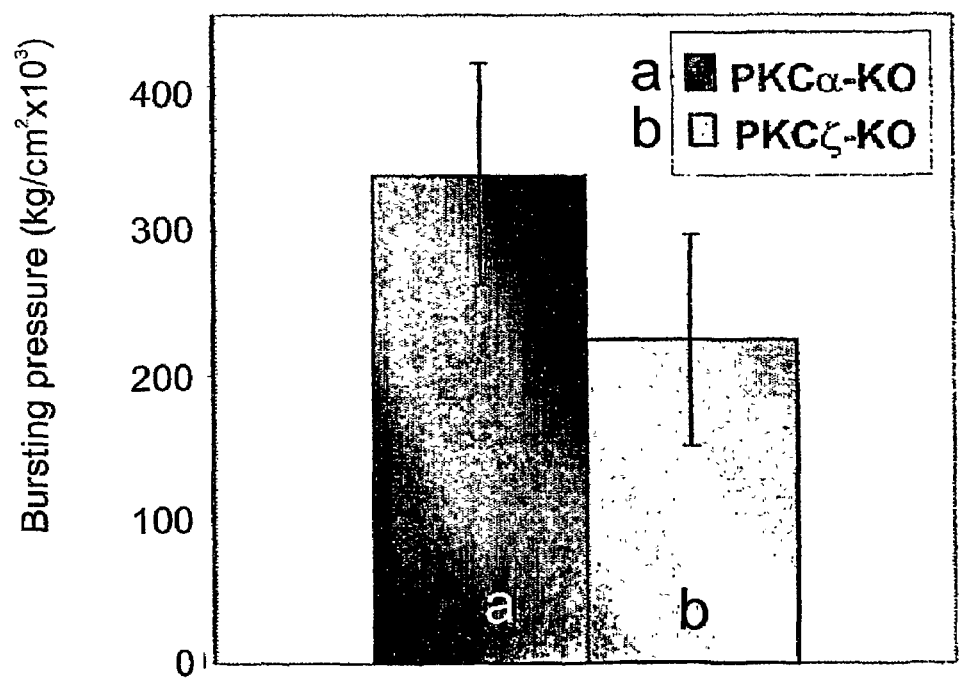

The importance of PKC isoforms in the wound healing process in vivo was established utilizing isoform specific PKC null mice. As seen in FIGS. 22A-B, when full thickness wounds were created on the back of PKCδ, PKCζ, PKCα null mice (knock-out, KO) and their wild type littermates, delayed wound healing was observed in PKCδ and PKCζ but not PKCα null mice. This data indicates that even in the absence of diabetic backgorund, specific PKC isoforms are essential for the wound healing process in skin.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their name and/or database accession numbers mentioned in this specification are herein incorporated in their entirety by reference into the specification, to the same extent as if each individual publication, patent, patent application or sequence was specifically and individually indicated to be incorporated herein by reference. In addition, citation or identification of any reference in this application shall not be construed as an admission that such reference is available as prior art to the present invention.

REFERENCES CITED BY NUMERALS

Aditional References are Cited in the Text

1. Hennings, H., Michael, D., Cheng, C., Steinert, P., Holbrook, K., and Yuspa, S. H. Calcium regulation of growth and differentiation of mouse epidermal cells in culture. Cell, 19: 245-254, 1980.

2. Yuspa, S. H., Kilkenny, A. E., Steinert, P. M., and Roop, D. R. Expression of murine epidermal differentiation markers is tightly regulated by restricted extracellular calcium concentrations in vitro. J.Cell Biol., 109: 1207-1217, 1989.

3. Fuchs, E. Epidermal differentiation: the bare essentials. J.Cell Biol., 111: 2807-2814, 1990.

4. Yuspa, S. H. The pathogenesis of squamous cell cancer: lessons learned from studies of skin carcinogenesis—Thirty-third G. H. A. Clowes Memorial Award Lecture. Cancer Res., 54:1178-1189, 1994.

5. Hennings, H. and Holbrook, K. A. Calcium regulation of cell-cell contact and differentiation of epidermal cells in culture. An ultrastructural study. Exp.Cell Res., 143: 127-142, 1983.

6. Tennenbaum, T., Li, L., Belanger, A. J., De Luca, L. M., and Yuspa, S. H. Selective changes in laminin adhesion and α6β4 integrin regulation are associated with the initial steps in keratinocyte maturation. Cell Growth Differ., 7: 615-628, 1996.

7. Tennenbaum, T., Belanger, A. J., Quaranta, V., and Yuspa, S. H. Differential regulation of integrins and extracellular matrix binding in epidermal differentiation and squamous tumor progression. J.Invest.Dermatol., 1: 157-161, 1996.

8. Nishizuka, Y. The molecular heterogeneity of PKC and its implications for cellular regulation. Nature, 334: 661-665, 1988.

9. Nishizuka, Y. The family of protein kinase C for signal transduction. JAMA, 262:1826-1833, 1989.

10. Denning, M. F., Dlugosz, A. A., Williams, E. K., Szallasi, Z., Blumberg, P. M., and Yuspa, S. H. Specific protein kinase C isozymes mediate the induction of keratinocyte differentiation markers by calcium. Cell Growth Differ., 6: 149-157, 1995.

11. Dlugosz, A. A., Pettit, G. R., and Yuspa, S. H. Involvement of Protein kinase C in $Ca^{2+}$-mediated differentiation on cultured primary mouse keratinocytes. J.Invest.Dermatol., 94: 519-519, 1990.(Abstract)

12. Dlugosz, A. A. and Yuspa, S. H. Coordinate changes in gene expression which mark the spinous to granular cell transition in epidermis are regulated by protein kinase C. J.Cell Biol., 120: 217-225, 1993.

13. Kuroki, T., Kashiwagi, M., Ishino, K., Huh, N., and Ohba, M. Adenovirus-mediated gene transfer to keratinocytes—a review. J.Investig.Dermatol.Symp.Proc., 4: 153-157, 1999.

14. Rosenfeld, M. A., Siegfried, W., Yoshimura, K., Yoneyama, K., Fukayama, M., Stier, L. E., Paakko, P. K., Gi, P., Stratford-Perricaudet, M., Jallet, J., Pavirani, A., Lecocq, J. P., and Crystal, R. G. Adenovirus-mediated transfer of a recombinant a1-antitrypsin gene to the lung epithelium in vivo. Science, 252: 431-434, 1991.

15. Setoguchi, Y., Jaffe, H. A., Danel, C., and Crystal, R. G. Ex Vivo and in vivo gene transfer to the skin using replication-deficient recombinant adenovirus vectors. J.Invest.Dermatol., 102: 415-421, 1994.

16. Greenhalgh, D. A., Rothnagel, J. A., and Roop, D. R. Epidermis: An attractive target tissue for gene therapy. J.Invest.Dermatol., 103: 63S-69S, 1994.

17. Miyake, S., Makimura, M., Kanegae, Y., Harada, S., Sato, Y., Takamori, K., Tokuda, C., and Saito, I. Efficient generation of recombinant adenoviruses using adenovirus DNA-terminal protein complex and a cosmid bearing the full-length virus genome. Proc.Natl.Acad.Sci.U.S.A., 93: 1320-1324, 1996.

18. Dlugosz, A. A., Glick, A. B., Tennenbaum, T., Weinberg, W. C., and Yuspa, S. H. Isolation and utilization of epidermal keratinocytes for oncogene research. In: P. K. Vogt and I. M. Verma (eds.), Methods in Enzymology, pp. 3-20, New York: Academic Press. 1995.

19. Ohba, M., Ishino, K., Kashiwagi, M., Kawabe, S., Chida, K., Huh, N. H., and Kuroki, T. Induction of differentiation in normal human keratinocytes by adenovirus-mediated introduction of the eta and delta isoforms of protein kinase C. Mol.Cell Biol., 18: 5199-5207, 1998.

20. Weinstein, M. L. Update on wound healing: a review of the literature. Mil.Med., 163: 620-624, 1998.

21. Singer, A. J. and Clark, R. A. Cutaneous wound healing. N.Engl.J.Med., 341: 738-746, 1999.

22. Whitby, D. J. and Ferguson, M. W. Immunohistochemical localization of growth factors in fetal wound healing. Dev.Biol., 147: 207-215, 1991.

23. Kiritsy, C. P., Lynch, B., and Lynch, S. E. Role of growth factors in cutaneous wound healing: a review. Crit.Rev.Oral Biol.Med., 4: 729-760, 1993.

24. Andresen, J. L., Ledet, T., and Ehlers, N. Keratocyte migration and peptide growth factors: the effect of PDGF, bFGF, EGF, IGF-I, aFGF and TGF-beta on human keratocyte migration in a collagen gel. Curr.Eye Res., 16: 605-613, 1997.

25. Werner, S., Breeden, M., Hubner, G., Greenhalgh, D. G., and Longaker, M. T. Induction of keratinocyte growth factor expression is reduced and delayed during wound healing in the genetically diabetic mouse. J.Invest.Dermatol., 103: 469-473, 1994.

26. Threadgill, D. W., Dlugosz, A. A., Hansen, L. A., Tennenbaum, T., Lichti, U., Yee, D., LaMantia, C., Mourton, T., Herrup, K., Harris, R. C., Barnard, J. A., Yuspa, S. H., Coffey, R. J., and Magnuson, T. Targeted disruption of mouse EGF receptor: effect of genetic background on mutant phenotype. Science, 269: 230-234, 1995.

27. Osada, S., Mizuno, K., Theo, T. C., Akita, Y., Suzuki, K., Kuroki, T., and Ohno, S. A phorbol ester receptor/protein kinase, nPKC$_\eta$, a new member of the protein kinase C family predominantly expressed in lung and skin. J.Biol.Chem., 265: 22434-22440, 1990.

28. Chida, K., Sagara, H., Suzuki, Y., Murakami, A., Osada, S., Ohno, S., Hirosawa, K., and Kuroki, T. The η isoform of protein kinase C is localized on rough endoplasmic reticulum. Mol.Cell Biol., 14: 3782-3790, 1994.

29. Knighton, D. R. and Fiegel, V. D. Growth factors and comprehensive surgical care of diabetic wounds. Curr.Opin.Gen.Surg., :32-9: 32-39, 1993.

30. Shaw, J. E. and Boulton, A. J. The pathogenesis of diabetic foot problems: an overview. Diabetes, 46*Suppl* 2:S58-61: S58-S611997.

31. Coghlan, M. P., Pillay, T. S., Tavare, J. M., and Siddle, K. Site-specific anti-phosphopeptide antibodies: use in assessing insulin receptor serine/threonine phosphorylation state and identification of serine-1327 as a novel site of phorbol ester-induced phosphorylation. Biochem.J., 303: 893-899, 1994.

32. Grunfeld, C. Diabetic foot ulcers: etiology, treatment, and prevention. Adv.Intern.Med., 37:103-32:103-132, 1992.

33. Reiber, G. E., Lipsky, B. A., and Gibbons, G. W., The burden of diabetic foot ulcers. Am.J.Surg., 176: 5S-10S, 1998.

34. Wertheimer, E., Trebicz, M., Eldar, T., Gartsbein, M., Nofeh-Mozes, S., and Tennenbaum, T. Differential Roles of Insulin Receptor and Insulin-Like Growth Factor-1 Receptor in Differentiation of Murine Skin Keratinocytes. J.Invest.Dermatol., in press: 2000.

35. Gschwendt, M. Protein kinase C delta. Eur.J.Biochem., 259: 555-564, 1999.

36. Bajou, K., Noel, A., Gerard, R. D., Masson, V., Brunner, N., Holst-Hansen, C., Skobe, M., Fusenig, N. E., Carmeliet, P., Collen, D., and Foidart, J. M. Absence of host plasminogen activator inhibitor 1 prevents cancer invasion and vascularization. Nat.Med., 4: 923-928, 1998.

37. Alessenko, A., Khan, W. A., Wetsel, W. C., and Hannun, Y. A. Selective changes in protein kinase C isoenzymes in rat liver nuclei during liver regeneration. Biochem.Biophys. Res.Commun., 182:1333-1339, 1992.

38. Soltoff, S. P. and Toker, A. Carbachol, substance P, and phorbol ester promote the tyrosine phosphorylation of protein kinase Cδ in salivary gland epithelial cells. J.Biol.Chem., 270: 13490-13495, 1995.

39. Mischak, H., Pierce, J. H., Goodnight, J., Kazanietz, M. G., Blumberg, P. M., and Mushinski, J. F. Phorbol ester-induced myeloid differentiation is mediated by protein kinase C-α and -δ and not by protein kinase C-βII, -ε, -zeta and eta. J.Biol.Chem., 268: 20110-20115, 1993.

40. Sun, Q., Tsutsumi, K., Kelleher, M. B., Pater, A., and Pater, M. M. Squamous metaplasia of normal and carcinoma in situ of HPV 16-immortalized human endocervical cells. Cancer Res., 52: 4254-4260, 1992.

41. Mischak, H., Goodnight, J., Kolch, W., Martiny-Baron, G., Schaechtle, C., Kazanietz, M. G., Blumberg, P. M., Pierce, J. H., and Mushinski, J. F. over-expression of protein kinase C-δ and -ε in NIH 3T3 cells induces opposite effects of growth, morphology, anchorage dependence, and tumorigenicity. J.Biol.Chem., 268: 6090-6096, 1993.

42. Braiman, L., Alt, A., Kuroki, T., Ohba, M., Bak, A., Tennenbaum, T., and Sampson, S. R. Protein kinase Cdelta mediates insulin-induced glucose transport in primary cultures of rat skeletal muscle. Mol.Endocrinol., 13: 2002-2012, 1999.

43. Braiman, L., Sheffi-Friedman, L., Bak, A., Tennenbaum, T., and Sampson, S. R. Tyrosine phosphorylation of specific protein kinase C isoenzymes participates in insulin stimulation of glucose transport in primary cultures of rat skeletal muscle. Diabetes, 48: 1922-1929, 1999.

44. Bandyopadhyay, G., Standaert, M. L., Kikkawa, U., Ono, Y., Moscat, J., and Farese, R. V. Effects of transiently expressed a typical (zeta, lambda), conventional (alpha, beta) and novel (delta, epsilon) protein kinase C isoforms on insulin-stimulated translocation of epitope-tagged GLUT4 glucose transporters in rat adipocytes: specific interchangeable effects of protein kinases C-zeta and C-lambda. Biochem.J., 337: 461-470, 1999.

45. Formisano, P., Oriente, F., Miele, C., Caruso, M., Auricchio, R., Vigliotta, G., Condorelli, G., and Beguinot, F. In NIH-3T3 fibroblasts, insulin receptor interaction with specific protein kinase C isoforms controls receptor intracellular routing. J.Biol.Chem., 273: 13197-13202, 1998.

46. Wang, Q. J., Bhattacharyya, D., Garfield, S., Nacro, K., Marquez, V. E., and Blumberg, P. M. Differential localization of protein kinase C delta by phorbol esters and related compounds using a fusion protein with green fluorescent protein. J.Biol.Chem., 274: 37233-37239, 1999.

What is claimed is:

1. A method of inducing or accelerating a healing of a skin wound, comprising administering at cells of the skin wound a nucleic acid construct which comprises a polynucleotide encoding a protein kinase C selected from the group consisting of PKC-δ, PKC-η, and PKC-ζ, operably linked to a promoter capable of directing transcription of said polynucleotide in said cells, whereby said cells produce a recombinant said protein kinase C thereby inducing or accelerating the healing process of the skin wound.

2. The method of claim 1, wherein said skin wound is selected from the group consisting of an ulcer, a burn, a laceration and a surgical incision.

3. The method of claim 1, wherein said ulcer is a diabetic ulcer.

* * * * *

UNITED STATES PATENT AND TRADEMARK OFFICE
CERTIFICATE OF CORRECTION

PATENT NO. : 7,402,571 B2
APPLICATION NO. : 10/169801
DATED : July 22, 2008
INVENTOR(S) : Tennenbaum et al.

It is certified that error appears in the above-identified patent and that said Letters Patent is hereby corrected as shown below:

On the cover page, item (73), replace "Shlomzlon" with -- Shlomzion --.

In the description, Col. 1, lines 7-8, replace "claims priority" with

-- is a continuation --;

Col. 1, line 7, replace "Jul." with -- July --; and

Col. 1, line 8, replace "Jul." with -- July --.

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,402,571 B2  
APPLICATION NO. : 10/169801  
DATED : July 22, 2008  
INVENTOR(S) : Tennenbaum et al.

Page 1 of 1

It is certified that error appears in the above-identified patent and that said Letters Patent is hereby corrected as shown below:

On the cover page, under Related U.S. Application Data (60), replace "Continuation" with --Continuation-in-part--.

In the description, Col. 1, lines 7-8, after "continuation", add

-- -in-part--.

Signed and Sealed this  
Fifth Day of July, 2011

David J. Kappos  
*Director of the United States Patent and Trademark Office*